United States Patent
Chen et al.

(10) Patent No.: US 9,109,208 B2
(45) Date of Patent: Aug. 18, 2015

(54) GENE, PROTEIN, PROTEIN COMPLEX AND METHOD FOR IMPROVING AROMA PRODUCTION IN A PLANT

(75) Inventors: Hong-Hwa Chen, Tainan (TW); Yu-Yun Hsiao, Tainan (TW); Wen-Chieh Tsai, Tainan (TW); Wen-Huei Chen, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 818 days.

(21) Appl. No.: 13/239,765

(22) Filed: Sep. 22, 2011

(65) Prior Publication Data

US 2013/0081152 A1    Mar. 28, 2013

(51) Int. Cl.
*C12N 9/10* (2006.01)
*C12N 5/14* (2006.01)
*C12N 15/82* (2006.01)

(52) U.S. Cl.
CPC .......... *C12N 9/1085* (2013.01); *C12N 15/8243* (2013.01); *C12N 5/14* (2013.01)

(58) Field of Classification Search
None
See application file for complete search history.

(56) References Cited

U.S. PATENT DOCUMENTS

2002/0106772 A1    8/2002    Croteau et al.

FOREIGN PATENT DOCUMENTS

TW    201004559    2/2010

OTHER PUBLICATIONS

Hsiao et al., A novel homodimeric geranyl diphosphate synthase from the orchid Phalaenopsis bellina lacking a DD(x)2-4D motif, 55 Plant J, 719-733 at 719-720, 723, 727(2008).*
Bouvier et al. (Molecular cloning of geranyl diphosphate synthase and compartmentation of monoterpene synthesis in plant cells, 24 Plant J No. 2, 241-252 (2000)).*
NCBI GenBank Accession Nos. Y17376 (published Nov. 22, 2000).*
NCBI GenBank Accession Nos. CAC16849 (published Nov. 22, 2000).*
Liang et al., Structure, mechanism and function of prenyltransferases, 269 Eur. J. Biochem., 3339-3354 at 3340-3342 (2002).*
Chris C. N. Van Schie et al., Geranyl diphosphate synthase is required for biosynthesis of gibberellins, The Plant Journal, 2007, pp. 752-762, vol. 52.
Kyozo Ogura et al., Enzymatic Aspects of Isoprenoid Chain Elongation, Chemical Reviews, Jun. 1998, pp. 1263-1276, vol. 98, No. 4.

K. Kinkead Reiling et al., Mono and Diterpene Production in *Escherichia coli*, Biotechnol Bioeng, 2004, pp. 200-212, vol. 87.
Charles C. Burke et al., Geranyl diphosphate synthase: Cloning, expression, and characterization of this prenyltransferase as a heterodimer, PNAS, Nov. 9, 1999, pp. 13062-13067, vol. 96, No. 23.
Florence Bouvier et al., Molecular cloning of geranyl diphosphate synthase and compartmentation of monoterpene synthesis in plant cells, The Plant Journal, 2000, pp. 241-252, vol. 24, No. 2.
Charles Burke et al., Geranyl diphosphate synthase from Abies grandis: cDNA isolation, functional expression, and characterization, Archives of Biochemistry and Biophysics, 2002, pp. 130-136, vol. 405.
Dorothea Tholl et al., Formation of Monoterpenes in *Antirrhinum majus* and *Clarkia breweri* Flowers Involves Heterodimeric Geranyl Diphosphate Synthases, The Plant Cell, Apr. 2004, pp. 977-992, vol. 16.
Yu-Yun Hsiao et al., A novel homodimeric geranyl diphosphate snthase from the orchid *Phalaenopsis bellina* lacking a DD(X)2-4D motif, The Plant Journal, 2008, p. 719-733, vol. 55.
Jorg Bohlmann et al., Terpenoid Secondary Metabolism in Arabidopsis thaliana: cDNA Cloning, Characterization, and Functional Expression of a Myrcene/ (E)-B-Ocimene Synthase, Archives of Biochemistry and Biophysics, Mar. 15, 2000, pp. 261-269, vol. 375, No. 2.
Charles Burke et al., Heteromeric geranyl diphosphate synthase from mint: construction of a functional fusion protein and inhibition by biosphosphonate substrate analogs, Archives of Biochemistry and Biophysics, 2004, pp. 52-60, vol. 422.
Yu-Yun Hsiao et al., Comparison of transcripts in *Phalaenopsis bellina* and *Phalaenopsis equestris* (Orchidaceae) flowers to deduce monoterpene biosynthesis pathway, Bmc Plant Biology, 2006, pp. 1-14, vol. 6, No. 14.
Charles Burke et al., Interaction with the Small Subunit of Geranyl Diphosphate Synthase Modifies the Chain Length Specificity of Geranylgeranyl Diphosphate Synthase to Produce Gernayl Diphosphate, The Journal of Biological Chemistry, Feb. 1, 2002, pp. 3141-3149, vol. 277, No. 5.
Kevin C. Wang et al., Isoprenyl diphosphate synthases, Biochimica et Biphysica Acta, 2000, pp. 33-48, vol. 1529.
Yu-Yun Hsiao et al., Studies on the biosynthesis pathway and its related genes of *Phalaenopsis bellina* floral scent, Dissertation Department of Life Sciences National Cheng Kung University, May 2008, pp. 1-134.
Yu-Yun Hsiao et al., A Novel Geranyl Diphosphate Synthase without an Asp-rich Motif Functioning as a Homodimer in a Plant, Taiwan Proteomics Society International Conference, 2007, pp. 123.
Yu-Yun Hsiao et al., Studies on the biosynthesis pathway and its related genes of *Phalaenopsis bellina* floral scent, Dissertation: Department of Life Sciences, National Cheng Kung University, 2008.

* cited by examiner

*Primary Examiner* — Brent T Page
*Assistant Examiner* — Matthew Keogh
(74) *Attorney, Agent, or Firm* — WPAT, P.C.; Anthony King

(57) ABSTRACT

The invention relates to a nucleic acid molecule that improves aroma production in a plant, and a cell and a transgenic plant comprising the nucleic acid molecule. A protein and a protein complex for catalyzing the synthesis of a monoterpene and a precursor thereof and uses for improving the production of aroma in a plant are also provided.

9 Claims, 7 Drawing Sheets

| Bait | Prey | |
|---|---|---|
| pGBKT7 | pGADT7 |  |
| Positive control | | |
| PeMADS4 | PeMADS6 | |
| Negative control | | |
| pGBKT7 | pGADT7 | |
| PbGDPS_SSU | PbGDPS_LSU | |
| PbGDPS_LSU | PbGDPS_SSU | |
| PbGDPS_SSU | PbGDPS_SSU | |
| PbGDPS_LSU | PbGDPS_LSU | |

SEQUENCE LISTING

<160> NUMBER OF SEQ ID NOS: 28

<210> SEQ ID NO 1
<211> LENGTH: 1071
<212> TYPE: DNA
<213> ORGANISM: Phalaenopsis bellina
<220> FEATURE:
<221> NAME/KEY: CDS
<222> LOCATION: (1)..(1071)

<400> SEQUENCE: 1

| | | | | | | | | | | | | | | | | |
|---|---|---|---|---|---|---|---|---|---|---|---|---|---|---|---|---|
| atg | gct | tcc | ttc | gcc | aca | ttt | cat | ctc | gca | ggt | tcc | cgt | cct | ctc | cgc | 48 |
| Met | Ala | Ser | Phe | Ala | Thr | Phe | His | Leu | Ala | Gly | Ser | Arg | Pro | Leu | Arg | |
| 1 | | | | 5 | | | | | 10 | | | | | 15 | | |

| cct | cct | ttc | ccg | act | cca | acc | atg | acc | gtc | ctc | cgt | ccc | cca | tcc | cgc | 96 |
|---|---|---|---|---|---|---|---|---|---|---|---|---|---|---|---|---|
| Pro | Pro | Phe | Pro | Thr | Pro | Thr | Met | Thr | Val | Leu | Arg | Pro | Pro | Ser | Arg | |
| | | | 20 | | | | | 25 | | | | | 30 | | | |

| tcc | ctt | ttc | ctc | tcc | ttc | cct | tcc | ctt | aac | gcg | gtt | gaa | atc | aag | gcc | 144 |
|---|---|---|---|---|---|---|---|---|---|---|---|---|---|---|---|---|
| Ser | Leu | Phe | Leu | Ser | Phe | Pro | Ser | Leu | Asn | Ala | Val | Glu | Ile | Lys | Ala | |
| | | 35 | | | | | 40 | | | | | 45 | | | | |

| gac | ccc | tct | gtt | gcc | aca | acc | gag | ttc | gat | ttc | aag | ggt | ttc | ttg | cta | 192 |
|---|---|---|---|---|---|---|---|---|---|---|---|---|---|---|---|---|
| Asp | Pro | Ser | Val | Ala | Thr | Thr | Glu | Phe | Asp | Phe | Lys | Gly | Phe | Leu | Leu | |
| 50 | | | | | 55 | | | | | 60 | | | | | | |

| aag | aag | gca | gaa | tcc | gta | aat | cga | gcc | cta | gat | ctc | gcg | att | ccc | gta | 240 |
|---|---|---|---|---|---|---|---|---|---|---|---|---|---|---|---|---|
| Lys | Lys | Ala | Glu | Ser | Val | Asn | Arg | Ala | Leu | Asp | Leu | Ala | Ile | Pro | Val | |
| 65 | | | | 70 | | | | | 75 | | | | | 80 | | |

| atc | cat | ccg | aag | cgt | atc | cac | gaa | gcg | atg | cga | tac | tcc | ctc | ctc | gca | 288 |
|---|---|---|---|---|---|---|---|---|---|---|---|---|---|---|---|---|
| Ile | His | Pro | Lys | Arg | Ile | His | Glu | Ala | Met | Arg | Tyr | Ser | Leu | Leu | Ala | |
| | | | | 85 | | | | | 90 | | | | | 95 | | |

| ggc | gga | aaa | cgc | atc | cgc | ccc | gtc | ctc | tgc | atc | gct | gct | tgc | gag | atc | 336 |
|---|---|---|---|---|---|---|---|---|---|---|---|---|---|---|---|---|
| Gly | Gly | Lys | Arg | Ile | Arg | Pro | Val | Leu | Cys | Ile | Ala | Ala | Cys | Glu | Ile | |
| | | | 100 | | | | | 105 | | | | | 110 | | | |

| gtc | ggc | ggc | gac | gag | gcc | caa | gcg | atc | ccc | cct | gcc | tgc | gcc | gtg | gag | 384 |
|---|---|---|---|---|---|---|---|---|---|---|---|---|---|---|---|---|
| Val | Gly | Gly | Asp | Glu | Ala | Gln | Ala | Ile | Pro | Pro | Ala | Cys | Ala | Val | Glu | |
| | | 115 | | | | | 120 | | | | | 125 | | | | |

| atg | att | cac | acc | atg | tct | ctt | atc | cac | gac | gat | ctc | cct | tgt | atg | gat | 432 |
|---|---|---|---|---|---|---|---|---|---|---|---|---|---|---|---|---|
| Met | Ile | His | Thr | Met | Ser | Leu | Ile | His | Asp | Asp | Leu | Pro | Cys | Met | Asp | |
| | 130 | | | | | 135 | | | | | 140 | | | | | |

| gac | gac | gat | ctg | cgg | cgc | ggt | atg | ccc | tcc | tgc | cac | cgc | gcg | tac | ggc | 480 |
|---|---|---|---|---|---|---|---|---|---|---|---|---|---|---|---|---|
| Asp | Asp | Asp | Leu | Arg | Arg | Gly | Met | Pro | Ser | Cys | His | Arg | Ala | Tyr | Gly | |
| 145 | | | | | 150 | | | | | 155 | | | | | 160 | |

| gaa | tcc | gtc | gcc | gtt | ttg | gct | gga | gac | gct | ctt | ctc | gca | ctc | gcc | ttc | 528 |
|---|---|---|---|---|---|---|---|---|---|---|---|---|---|---|---|---|
| Glu | Ser | Val | Ala | Val | Leu | Ala | Gly | Asp | Ala | Leu | Leu | Ala | Leu | Ala | Phe | |
| | | | | 165 | | | | | 170 | | | | | 175 | | |

| caa | cat | ctg | gtt | gat | ctc | cgt | aac | tac | cct | tca | tcc | atc | gcg | atc | ccc | 576 |
|---|---|---|---|---|---|---|---|---|---|---|---|---|---|---|---|---|
| Gln | His | Leu | Val | Asp | Leu | Arg | Asn | Tyr | Pro | Ser | Ser | Ile | Ala | Ile | Pro | |
| | | | 180 | | | | | 185 | | | | | 190 | | | |

| cct | gca | atc | ttg | gtc | cgt | gcc | acg | gcg | gag | ctc | gcc | cgc | tgc | atc | ggc | 624 |
|---|---|---|---|---|---|---|---|---|---|---|---|---|---|---|---|---|
| Pro | Ala | Ile | Leu | Val | Arg | Ala | Thr | Ala | Glu | Leu | Ala | Arg | Cys | Ile | Gly | |
| | | 195 | | | | | 200 | | | | | 205 | | | | |

| acg | gag | ggt | ctg | gtc | gcc | ggt | cag | tta | ctc | gac | atg | gaa | tcc | acc | ggc | 672 |
|---|---|---|---|---|---|---|---|---|---|---|---|---|---|---|---|---|
| Thr | Glu | Gly | Leu | Val | Ala | Gly | Gln | Leu | Leu | Asp | Met | Glu | Ser | Thr | Gly | |
| | 210 | | | | | 215 | | | | | 220 | | | | | |

| ctg | gaa | gat | ccc | gtc | gac | att | gat | cgc | ctc | gag | ttc | atc | cac | ttg | cat | 720 |
|---|---|---|---|---|---|---|---|---|---|---|---|---|---|---|---|---|
| Leu | Glu | Asp | Pro | Val | Asp | Ile | Asp | Arg | Leu | Glu | Phe | Ile | His | Leu | His | |
| 225 | | | | | 230 | | | | | 235 | | | | | 240 | |

| aaa | acc | gcc | gcg | ctg | ctc | gag | gct | tcg | gtg | gtg | atc | ggc | gca | gtg | gtc | 768 |
|---|---|---|---|---|---|---|---|---|---|---|---|---|---|---|---|---|
| Lys | Thr | Ala | Ala | Leu | Leu | Glu | Ala | Ser | Val | Val | Ile | Gly | Ala | Val | Val | |
| | | | | 245 | | | | | 250 | | | | | 255 | | |

| ggc | gga | gga | tcg | gat | tca | gag | gtc | gag | cgg | ttg | cgg | cgt | tat | gcc | cga | 816 |
|---|---|---|---|---|---|---|---|---|---|---|---|---|---|---|---|---|
| Gly | Gly | Gly | Ser | Asp | Ser | Glu | Val | Glu | Arg | Leu | Arg | Arg | Tyr | Ala | Arg | |

```
            260                 265                 270
tgc atc gga tta ctt ttc cag gtg gtg gat gat att ctc gat gtg acc       864
Cys Ile Gly Leu Leu Phe Gln Val Val Asp Asp Ile Leu Asp Val Thr
        275                 280                 285 aaa tcg tcg cag gag ctg ggg aaa act gct gcc aag gat ttg gct agc       912
Lys Ser Ser Gln Glu Leu Gly Lys Thr Ala Ala Lys Asp Leu Ala Ser
290                 295                 300 aac aag aca acc tac cct aag ctt ttg ggg ctg gag aag tcc agg gag       960
Asn Lys Thr Thr Tyr Pro Lys Leu Leu Gly Leu Glu Lys Ser Arg Glu
305                 310                 315                 320 ttt gcc gac gaa ctt ctc cgc gat gct aag tca cag att gag ggt ttt      1008
Phe Ala Asp Glu Leu Leu Arg Asp Ala Lys Ser Gln Ile Glu Gly Phe
                325                 330                 335 gat tct ttg aaa gct gcg cca tta ctc cac ctt gcg aat tac atc gct      1056
Asp Ser Leu Lys Ala Ala Pro Leu Leu His Leu Ala Asn Tyr Ile Ala
            340                 345                 350 tac agg cag aat taa                                                  1071
Tyr Arg Gln Asn
        355
```

<210> SEQ ID NO 2
<211> LENGTH: 356
<212> TYPE: PRT
<213> ORGANISM: Phalaenopsis bellina

<400> SEQUENCE: 2

```
Met Ala Ser Phe Ala Thr Phe His Leu Ala Gly Ser Arg Pro Leu Arg
1               5                   10                  15

Pro Pro Phe Pro Thr Pro Thr Met Thr Val Leu Arg Pro Pro Ser Arg
            20                  25                  30

Ser Leu Phe Leu Ser Phe Pro Ser Leu Asn Ala Val Glu Ile Lys Ala
        35                  40                  45

Asp Pro Ser Val Ala Thr Thr Glu Phe Asp Phe Lys Gly Phe Leu Leu
    50                  55                  60

Lys Lys Ala Glu Ser Val Asn Arg Ala Leu Asp Leu Ala Ile Pro Val
65                  70                  75                  80

Ile His Pro Lys Arg Ile His Glu Ala Met Arg Tyr Ser Leu Leu Ala
                85                  90                  95

Gly Gly Lys Arg Ile Arg Pro Val Leu Cys Ile Ala Ala Cys Glu Ile
            100                 105                 110

Val Gly Gly Asp Glu Ala Gln Ala Ile Pro Pro Ala Cys Ala Val Glu
        115                 120                 125

Met Ile His Thr Met Ser Leu Ile His Asp Asp Leu Pro Cys Met Asp
    130                 135                 140

Asp Asp Asp Leu Arg Arg Gly Met Pro Ser Cys His Arg Ala Tyr Gly
145                 150                 155                 160

Glu Ser Val Ala Val Leu Ala Gly Asp Ala Leu Leu Ala Leu Ala Phe
                165                 170                 175

Gln His Leu Val Asp Leu Arg Asn Tyr Pro Ser Ser Ile Ala Ile Pro
            180                 185                 190

Pro Ala Ile Leu Val Arg Ala Thr Ala Glu Leu Ala Arg Cys Ile Gly
        195                 200                 205

Thr Glu Gly Leu Val Ala Gly Gln Leu Leu Asp Met Glu Ser Thr Gly
    210                 215                 220

Leu Glu Asp Pro Val Asp Ile Asp Arg Leu Glu Phe Ile His Leu His
225                 230                 235                 240
```

```
Lys Thr Ala Ala Leu Leu Glu Ala Ser Val Ile Gly Ala Val Val
                245                 250                 255

Gly Gly Gly Ser Asp Ser Glu Val Glu Arg Leu Arg Arg Tyr Ala Arg
        260                 265                 270

Cys Ile Gly Leu Leu Phe Gln Val Val Asp Asp Ile Leu Asp Val Thr
            275                 280                 285

Lys Ser Ser Gln Glu Leu Gly Lys Thr Ala Ala Lys Asp Leu Ala Ser
        290                 295                 300

Asn Lys Thr Thr Tyr Pro Lys Leu Leu Gly Leu Glu Lys Ser Arg Glu
305                 310                 315                 320

Phe Ala Asp Glu Leu Leu Arg Asp Ala Lys Ser Gln Ile Glu Gly Phe
                325                 330                 335

Asp Ser Leu Lys Ala Ala Pro Leu Leu His Leu Ala Asn Tyr Ile Ala
            340                 345                 350

Tyr Arg Gln Asn
        355

<210> SEQ ID NO 3
<211> LENGTH: 1102
<212> TYPE: DNA
<213> ORGANISM: Phalaenopsis bellina
<220> FEATURE:
<221> NAME/KEY: CDS
<222> LOCATION: (14)..(787)

<400> SEQUENCE: 3
aaacccaaaa aaa atg gca gca atc ttt ccc tca atc ccc tcc aat ttc        49
            Met Ala Ala Ile Phe Pro Ser Ile Pro Ser Asn Phe
              1               5                  10 aaa cca cct caa atc tcc caa acc cta act cgc cgg cgg cga ccc aat       97
Lys Pro Pro Gln Ile Ser Gln Thr Leu Thr Arg Arg Arg Arg Pro Asn
         15                  20                  25 cga acc ctc tgc acc gcc acc tcc gat caa tcc tat ctc tcc gca tcg      145
Arg Thr Leu Cys Thr Ala Thr Ser Asp Gln Ser Tyr Leu Ser Ala Ser
 30                  35                  40 agc gcc gac ata tat tcc cat ctc ctc cgc agc ctc ccc gcc acc att      193
Ser Ala Asp Ile Tyr Ser His Leu Leu Arg Ser Leu Pro Ala Thr Ile
45                  50                  55                  60 cac ccc tcc gtc aaa gcc ccg atc cac agc ctc ctc tct tcc ccc att      241
His Pro Ser Val Lys Ala Pro Ile His Ser Leu Leu Ser Ser Pro Ile
                 65                  70                  75 cct ccg acc atc gcc cct ccc ctc tgc ctc gcc gcc acc gaa ctc gtc      289
Pro Pro Thr Ile Ala Pro Pro Leu Cys Leu Ala Ala Thr Glu Leu Val
         80                  85                  90 ggc gga aac ccg aac tcc gcc atc aac gcc gcc tgc gcg atc cac ctc      337
Gly Gly Asn Pro Asn Ser Ala Ile Asn Ala Ala Cys Ala Ile His Leu
     95                 100                 105 atc cac gcc gtc acc cac acc cgc acc gcc cct ccc ctc gcc gaa ttc      385
Ile His Ala Val Thr His Thr Arg Thr Ala Pro Pro Leu Ala Glu Phe
110                 115                 120 tcc ccc gga gta ctg ctc atg acc gga gac ggg ctt ctg gtt cta gcg      433
Ser Pro Gly Val Leu Leu Met Thr Gly Asp Gly Leu Leu Val Leu Ala
125                 130                 135                 140 tat gaa atg ctg gct cga tcg ccg gcg gtt gat gcg gac acc tcc gtt      481
Tyr Glu Met Leu Ala Arg Ser Pro Ala Val Asp Ala Asp Thr Ser Val
                145                 150                 155 agg gtg ctg aag gag gtg gcg aga acg gcg gct gcc gtc gcg gcg gcg      529
Arg Val Leu Lys Glu Val Ala Arg Thr Ala Ala Ala Val Ala Ala Ala
            160                 165                 170
```

```
tat gag ggg ggg agg gag ggg gag ctg gcg gcc ggt gcg gcg gcg tgc     577
Tyr Glu Gly Gly Arg Glu Gly Glu Leu Ala Ala Gly Ala Ala Ala Cys
            175                 180                 185 ggg gtt ata ttg gga gga ggg aat gag gag gag gtg gag agg ggg agg     625
Gly Val Ile Leu Gly Gly Gly Asn Glu Glu Glu Val Glu Arg Gly Arg
        190                 195                 200 agg gtg ggg atg ttt gcc gga aag atg gag ctg gtg gag gcg gag gtg     673
Arg Val Gly Met Phe Ala Gly Lys Met Glu Leu Val Glu Ala Glu Val
205                 210                 215                 220 gag ttg cgg cta ggg ttt gaa gac gcg aag gcc ggt gcg gtt agg cga     721
Glu Leu Arg Leu Gly Phe Glu Asp Ala Lys Ala Gly Ala Val Arg Arg
                225                 230                 235 ctg ctt gag gag atg cgt ttc act caa agt ttt gtt aat gta aga aat     769
Leu Leu Glu Glu Met Arg Phe Thr Gln Ser Phe Val Asn Val Arg Asn
            240                 245                 250 cct ttt tat ggg aaa taa tatatatata ttgtttattt taaatttata            817
Pro Phe Tyr Gly Lys
                255 ttataattta aaaaaacaaa tattagatga agtggtggcg gtgtgccaac aaatattacg    877 tcaggactct gggcatagag atacgttcgg agttcaataa aatcacgtca cctggaggtg    937 acaaaaaaat aaaaaaataa actcatttta gcataaggaa atattctccg gtattatttc    997 acgttatcca agtattattg tggtgatatt catgtattat tgtattctga gaatattccc   1057 ggtgttataa taaacaata ttatatcaaa aaaaaaaaaa aaaaa                    1102

<210> SEQ ID NO 4
<211> LENGTH: 257
<212> TYPE: PRT
<213> ORGANISM: Phalaenopsis bellina

<400> SEQUENCE: 4

Met Ala Ala Ile Phe Pro Ser Ile Pro Ser Asn Phe Lys Pro Pro Gln
1               5                   10                  15

Ile Ser Gln Thr Leu Thr Arg Arg Arg Pro Asn Arg Thr Leu Cys
            20                  25                  30

Thr Ala Thr Ser Asp Gln Ser Tyr Leu Ser Ala Ser Ser Ala Asp Ile
        35                  40                  45

Tyr Ser His Leu Leu Arg Ser Leu Pro Ala Thr Ile His Pro Ser Val
    50                  55                  60

Lys Ala Pro Ile His Ser Leu Leu Ser Ser Pro Ile Pro Pro Thr Ile
65                  70                  75                  80

Ala Pro Pro Leu Cys Leu Ala Thr Glu Leu Val Gly Gly Asn Pro
                85                  90                  95

Asn Ser Ala Ile Asn Ala Ala Cys Ala Ile His Leu Ile His Ala Val
            100                 105                 110

Thr His Thr Arg Thr Ala Pro Pro Leu Ala Glu Phe Ser Pro Gly Val
        115                 120                 125

Leu Leu Met Thr Gly Asp Gly Leu Leu Val Leu Ala Tyr Glu Met Leu
    130                 135                 140

Ala Arg Ser Pro Ala Val Asp Ala Asp Thr Ser Val Arg Val Leu Lys
145                 150                 155                 160

Glu Val Ala Arg Thr Ala Ala Ala Val Ala Ala Tyr Glu Gly Gly
                165                 170                 175

Arg Glu Gly Glu Leu Ala Ala Gly Ala Ala Ala Cys Gly Val Ile Leu
            180                 185                 190

Gly Gly Gly Asn Glu Glu Glu Val Glu Arg Gly Arg Arg Val Gly Met
```

```
            195                 200                 205
        Phe Ala Gly Lys Met Glu Leu Val Glu Ala Glu Val Glu Leu Arg Leu
            210                 215                 220
        Gly Phe Glu Asp Ala Lys Ala Gly Ala Val Arg Arg Leu Leu Glu Glu
        225                 230                 235                 240
        Met Arg Phe Thr Gln Ser Phe Val Asn Val Arg Asn Pro Phe Tyr Gly
                        245                 250                 255
        Lys

<210> SEQ ID NO 5
<211> LENGTH: 27
<212> TYPE: DNA
<213> ORGANISM: artificial
<220> FEATURE:
<223> OTHER INFORMATION: primer

<400> SEQUENCE: 5
cgaggaggga gtatcgcatc gcttcgt                                       27

<210> SEQ ID NO 6
<211> LENGTH: 28
<212> TYPE: DNA
<213> ORGANISM: artificial
<220> FEATURE:
<223> OTHER INFORMATION: primer

<400> SEQUENCE: 6
cacaccatgt ctctcatcca cgacgatc                                      28

<210> SEQ ID NO 7
<211> LENGTH: 29
<212> TYPE: DNA
<213> ORGANISM: artificial
<220> FEATURE:
<223> OTHER INFORMATION: primer

<400> SEQUENCE: 7
caccatgccc tctgttgcca caaccgagt                                     29

<210> SEQ ID NO 8
<211> LENGTH: 28
<212> TYPE: DNA
<213> ORGANISM: artificial
<220> FEATURE:
<223> OTHER INFORMATION: primer

<400> SEQUENCE: 8
attctgcctg taagcgatgt aattcgca                                      28

<210> SEQ ID NO 9
<211> LENGTH: 20
<212> TYPE: DNA
<213> ORGANISM: artificial
<220> FEATURE:
<223> OTHER INFORMATION: primer

<400> SEQUENCE: 9
ggctagcaac aagacaacct                                               20

<210> SEQ ID NO 10
<211> LENGTH: 20
<212> TYPE: DNA
<213> ORGANISM: artificial
<220> FEATURE:
```

<223> OTHER INFORMATION: primer

<400> SEQUENCE: 10
gaaatttgaa gcagcctagc                                      20

<210> SEQ ID NO 11
<211> LENGTH: 381
<212> TYPE: PRT
<213> ORGANISM: Abies grandis

<400> SEQUENCE: 11

```
Met Ala Tyr Ser Ala Met Ala Thr Met Gly Tyr Asn Gly Met Ala Ala
1               5                   10                  15

Ser Cys His Thr Leu His Pro Thr Ser Pro Leu Lys Pro Phe His Gly
            20                  25                  30

Ala Ser Thr Ser Leu Glu Ala Phe Asn Gly Glu His Met Gly Leu Leu
        35                  40                  45

Arg Gly Tyr Ser Lys Arg Lys Leu Ser Ser Tyr Lys Asn Pro Ala Ser
    50                  55                  60

Arg Ser Ser Asn Ala Thr Val Ala Gln Leu Leu Asn Pro Pro Gln Lys
65                  70                  75                  80

Gly Lys Lys Ala Val Glu Phe Asp Phe Asn Lys Tyr Met Asp Ser Lys
                85                  90                  95

Ala Met Thr Val Asn Glu Ala Leu Asn Lys Ala Ile Pro Leu Arg Tyr
            100                 105                 110

Pro Gln Lys Ile Tyr Glu Ser Met Arg Tyr Ser Leu Leu Ala Gly Gly
        115                 120                 125

Lys Arg Val Arg Pro Val Leu Cys Ile Ala Ala Cys Glu Leu Val Gly
    130                 135                 140

Gly Thr Glu Glu Leu Ala Ile Pro Thr Ala Cys Ala Ile Glu Met Ile
145                 150                 155                 160

His Thr Met Ser Leu Met His Asp Asp Leu Pro Cys Ile Asp Asn Asp
                165                 170                 175

Asp Leu Arg Arg Gly Lys Pro Thr Asn His Lys Ile Phe Gly Glu Asp
            180                 185                 190

Thr Ala Val Thr Ala Gly Asn Ala Leu His Ser Tyr Ala Phe Glu His
        195                 200                 205

Ile Ala Val Ser Thr Ser Lys Thr Val Gly Ala Asp Arg Ile Leu Arg
    210                 215                 220

Met Val Ser Glu Leu Gly Arg Ala Thr Gly Ser Glu Gly Val Met Gly
225                 230                 235                 240

Gly Gln Met Val Asp Ile Ala Ser Glu Gly Asp Pro Ser Ile Asp Leu
                245                 250                 255

Gln Thr Leu Glu Trp Ile His Ile His Lys Thr Ala Met Leu Leu Glu
            260                 265                 270

Cys Ser Val Val Cys Gly Ala Ile Ile Gly Gly Ala Ser Glu Ile Val
        275                 280                 285

Ile Glu Arg Ala Arg Arg Tyr Ala Arg Cys Val Gly Leu Leu Phe Gln
    290                 295                 300

Val Val Asp Asp Ile Leu Asp Val Thr Lys Ser Ser Asp Glu Leu Gly
305                 310                 315                 320

Lys Thr Ala Gly Lys Asp Leu Ile Ser Asp Lys Ala Thr Tyr Pro Lys
                325                 330                 335

Leu Met Gly Leu Glu Lys Ala Lys Glu Phe Ser Asp Glu Leu Leu Asn
            340                 345                 350
```

Arg Ala Lys Gly Glu Leu Ser Cys Phe Asp Pro Val Lys Ala Ala Pro
        355                 360                 365

Leu Leu Gly Leu Ala Asp Tyr Val Ala Phe Arg Gln Asn
    370                 375                 380

<210> SEQ ID NO 12
<211> LENGTH: 387
<212> TYPE: PRT
<213> ORGANISM: Abies grandis

<400> SEQUENCE: 12

Met Ala Tyr Ser Gly Met Val Arg Ser Phe Gln Gly Val Tyr Phe Met
1               5                   10                  15

Ala Val Ala Leu Asp Arg Asn Arg Asn Leu Lys Arg Ile Asp Ile Pro
            20                  25                  30

Ser Lys Arg Phe Asp Gly Val Ser Thr Ser Phe Val Ala Cys Asn Gly
        35                  40                  45

Glu His Leu Gly Leu Pro Val Asn Leu Lys Lys Glu Phe Leu Ser Cys
    50                  55                  60

Ile Gln Arg Ala Ser Ser Arg Ser Ser Asn Thr Ile Val Gln Phe
65                  70                  75                  80

Ala Asn Leu Pro Glu Gln Gly Lys Lys Val Val Glu Phe Asp Phe Asn
                85                  90                  95

Lys Tyr Met Leu Ser Lys Ala Met Ala Val Thr Glu Ala Leu Asp Lys
            100                 105                 110

Ala Ile Pro His Ser Tyr Pro Gln Lys Ile His Glu Ser Met Arg Tyr
        115                 120                 125

Ser Leu Leu Ala Gly Gly Lys Arg Val Arg Pro Val Leu Cys Ile Ala
    130                 135                 140

Ala Cys Glu Leu Val Gly Gly Arg Glu Glu Leu Ala Met Pro Thr Ala
145                 150                 155                 160

Cys Ala Met Glu Met Ile His Thr Met Ser Leu Ile His Asp Asp Leu
                165                 170                 175

Pro Cys Met Asp Asn Asp Asp Leu Arg Arg Gly Lys Pro Thr Asn His
            180                 185                 190

Lys Val Phe Gly Gln Asp Thr Ala Leu Leu Ala Gly Asp Ala Leu His
        195                 200                 205

Ala Phe Ala Phe Glu His Ile Val Ala Phe Thr Ser Lys Ser Val Gly
    210                 215                 220

Ser Asp Gly Ile Leu Arg Ala Val Thr Glu Leu Ala Arg Ala Thr Gly
225                 230                 235                 240

Pro Gln Gly Ile Met Gly Gly Gln Ile Val Asp Ile Ala Ser Glu Arg
                245                 250                 255

Asp Ala Phe Val Asp Leu Gln Thr Leu Glu Trp Ile His Ile His Lys
            260                 265                 270

Thr Ala Val Leu Phe Glu Cys Ala Thr Val Cys Gly Ala Ile Ile Gly
        275                 280                 285

Gly Ala Ser Gly Asp Glu Ile Glu Arg Ile Arg Arg Phe Ala Arg Tyr
    290                 295                 300

Leu Gly Leu Leu Phe Gln Val Val Asp Asp Ile Leu Asp Val Thr Lys
305                 310                 315                 320

Ser Ser Glu Asp Leu Gly Lys Thr Ala Gly Lys Asp Leu Val Ser Asp
                325                 330                 335

Lys Ala Thr Tyr Pro Lys Leu Met Gly Leu Glu Lys Ala Lys Gly Phe

```
                    340                 345                 350
Ser Leu Glu Leu Leu Asn Lys Ala Lys Glu Glu Leu Ser Cys Phe Asp
            355                 360                 365

Pro Met Lys Ala Ala Pro Leu Phe Gly Leu Ala Asp Tyr Met Ala Leu
            370                 375                 380

Arg Gln Asn
385

<210> SEQ ID NO 13
<211> LENGTH: 372
<212> TYPE: PRT
<213> ORGANISM: Antirrhinum majus

<400> SEQUENCE: 13

Met Ser Leu Val Asn Pro Ile Thr Thr Trp Ser Thr Thr Thr Thr Ser
1               5                   10                  15

Lys Ser Pro Lys Asn Val Gln Thr Thr Thr Arg Ser Arg Ser Ile Ile
            20                  25                  30

Leu Pro His Lys Ile Ser Leu Phe Pro Ser Asn Pro Lys Ser Lys Ser
        35                  40                  45

Lys Thr His Leu Arg Phe Ser Ile Ser Ser Ile Leu Thr Lys Asn Pro
50                  55                  60

Gln Glu Ser Ser Gln Lys Thr Ser Lys Asp Pro Thr Phe Thr Leu Asp
65                  70                  75                  80

Phe Lys Thr Tyr Met Leu Glu Lys Ala Ser Ser Val Asn Lys Ala Leu
                85                  90                  95

Glu Gln Ala Val Leu Leu Lys Glu Pro Leu Lys Ile His Glu Ser Met
            100                 105                 110

Arg Tyr Ser Leu Leu Ala Gly Gly Lys Arg Val Arg Pro Met Leu Cys
        115                 120                 125

Ile Ala Ala Cys Glu Leu Val Gly Gly Leu Glu Ser Thr Ala Met Pro
130                 135                 140

Ser Ala Cys Ala Val Glu Met Ile His Thr Met Ser Leu Ile His Asp
145                 150                 155                 160

Asp Leu Pro Cys Met Asp Asn Asp Asp Leu Arg Arg Gly Lys Pro Thr
                165                 170                 175

Asn His Lys Ile Tyr Gly Glu Asp Val Ala Val Leu Ala Gly Asp Ala
            180                 185                 190

Leu Leu Ala Phe Ser Phe Glu His Val Ala Lys Ser Thr Lys Gly Val
        195                 200                 205

Ser Ser Asp Arg Ile Val Arg Val Ile Gly Glu Leu Ala Lys Cys Ile
210                 215                 220

Gly Ser Glu Gly Leu Val Ala Gly Gln Val Val Asp Ile Ser Ser Glu
225                 230                 235                 240

Gly Met Thr Glu Val Gly Leu Glu His Leu Glu Phe Ile His Val His
                245                 250                 255

Lys Thr Ala Ala Leu Leu Glu Ala Ser Val Val Leu Gly Ala Ile Val
            260                 265                 270

Gly Gly Ala Asp Asp Glu Asp Val Glu Lys Leu Arg Lys Phe Ala Arg
        275                 280                 285

Cys Ile Gly Leu Leu Phe Gln Val Val Asp Asp Ile Leu Asp Val Thr
290                 295                 300

Lys Ser Ser Gln Glu Leu Gly Lys Thr Ala Gly Lys Asp Leu Val Ala
305                 310                 315                 320
```

```
Asp Lys Thr Thr Tyr Pro Lys Leu Leu Gly Ile Glu Lys Ser Arg Glu
            325                 330                 335

Phe Ala Glu Lys Leu Asn Arg Glu Ala Gln Glu Gln Leu Glu Gly Phe
        340                 345                 350

Asp Ser Val Lys Ala Ala Pro Leu Ile Ala Leu Ala Asn Tyr Ile Ala
        355                 360                 365

Tyr Arg Asp Asn
        370

<210> SEQ ID NO 14
<211> LENGTH: 377
<212> TYPE: PRT
<213> ORGANISM: Mentha piperita

<400> SEQUENCE: 14

Met Ser Ala Leu Val Asn Pro Val Ala Lys Trp Pro Gln Thr Ile Gly
1               5                   10                  15

Val Lys Asp Val His Gly Gly Arg Arg Arg Ser Arg Ser Thr Leu
            20                  25                  30

Phe Gln Ser His Pro Leu Arg Thr Glu Met Pro Phe Ser Leu Tyr Phe
        35                  40                  45

Ser Ser Pro Leu Lys Ala Pro Ala Thr Phe Ser Val Ser Ala Val Tyr
    50                  55                  60

Thr Lys Glu Gly Ser Glu Ile Arg Asp Lys Asp Pro Ala Pro Ser Thr
65                  70                  75                  80

Ser Pro Ala Phe Asp Phe Asp Gly Tyr Met Leu Arg Lys Ala Lys Ser
                85                  90                  95

Val Asn Lys Ala Leu Glu Ala Ala Val Gln Met Lys Glu Pro Leu Lys
            100                 105                 110

Ile His Glu Ser Met Arg Tyr Ser Leu Leu Ala Gly Gly Lys Arg Val
        115                 120                 125

Arg Pro Met Leu Cys Ile Ala Ala Cys Glu Leu Val Gly Gly Asp Glu
    130                 135                 140

Ser Thr Ala Met Pro Ala Ala Cys Ala Val Glu Met Ile His Thr Met
145                 150                 155                 160

Ser Leu Met His Asp Asp Leu Pro Cys Met Asp Asn Asp Asp Leu Arg
                165                 170                 175

Arg Gly Lys Pro Thr Asn His Met Ala Phe Gly Glu Ser Val Ala Val
            180                 185                 190

Leu Ala Gly Asp Ala Leu Leu Ser Phe Ala Phe Glu His Val Ala Ala
        195                 200                 205

Ala Thr Lys Gly Ala Pro Pro Glu Arg Ile Val Arg Val Leu Gly Glu
    210                 215                 220

Leu Ala Val Ser Ile Gly Ser Glu Gly Leu Val Ala Gly Gln Val Val
225                 230                 235                 240

Asp Val Cys Ser Glu Gly Met Ala Glu Val Gly Leu Asp His Leu Glu
                245                 250                 255

Phe Ile His His His Lys Thr Ala Ala Leu Leu Gln Gly Ser Val Val
            260                 265                 270

Leu Gly Ala Ile Leu Gly Gly Gly Lys Glu Glu Val Ala Lys Leu
        275                 280                 285

Arg Lys Phe Ala Asn Cys Ile Gly Leu Leu Phe Gln Val Val Asp Asp
    290                 295                 300

Ile Leu Asp Val Thr Lys Ser Ser Lys Glu Leu Gly Lys Thr Ala Gly
305                 310                 315                 320
```

-continued

```
Lys Asp Leu Val Ala Asp Lys Thr Thr Tyr Pro Lys Leu Ile Gly Val
                325                 330                 335

Glu Lys Ser Lys Glu Phe Ala Asp Arg Leu Asn Arg Glu Ala Gln Glu
            340                 345                 350

Gln Leu Leu His Phe His Pro His Arg Ala Ala Pro Leu Ile Ala Leu
        355                 360                 365

Ala Asn Tyr Ile Ala Tyr Arg Asp Asn
    370                 375

<210> SEQ ID NO 15
<211> LENGTH: 356
<212> TYPE: PRT
<213> ORGANISM: Phalaenopsis bellina

<400> SEQUENCE: 15

Met Ala Ser Phe Ala Thr Phe His Leu Ala Gly Ser Arg Pro Leu Arg
1               5                   10                  15

Pro Pro Phe Pro Thr Pro Thr Met Thr Val Leu Arg Pro Pro Ser Arg
            20                  25                  30

Ser Leu Phe Leu Ser Phe Pro Ser Leu Asn Ala Val Glu Ile Lys Ala
        35                  40                  45

Asp Pro Ser Val Ala Thr Thr Glu Phe Asp Phe Lys Gly Phe Leu Leu
    50                  55                  60

Lys Lys Ala Glu Ser Val Asn Arg Ala Leu Asp Leu Ala Ile Pro Val
65                  70                  75                  80

Ile His Pro Lys Arg Ile His Glu Ala Met Arg Tyr Ser Leu Leu Ala
                85                  90                  95

Gly Gly Lys Arg Ile Arg Pro Val Leu Cys Ile Ala Ala Cys Glu Ile
            100                 105                 110

Val Gly Gly Asp Glu Ala Gln Ala Ile Pro Pro Ala Cys Ala Val Glu
        115                 120                 125

Met Ile His Thr Met Ser Leu Ile His Asp Asp Leu Pro Cys Met Asp
    130                 135                 140

Asp Asp Asp Leu Arg Arg Gly Met Pro Ser Cys His Arg Ala Tyr Gly
145                 150                 155                 160

Glu Ser Val Ala Val Leu Ala Gly Asp Ala Leu Leu Ala Leu Ala Phe
                165                 170                 175

Gln His Leu Val Asp Leu Arg Asn Tyr Pro Ser Ser Ile Ala Ile Pro
            180                 185                 190

Pro Ala Ile Leu Val Arg Ala Thr Ala Glu Leu Ala Arg Cys Ile Gly
        195                 200                 205

Thr Glu Gly Leu Val Ala Gly Gln Leu Leu Asp Met Glu Ser Thr Gly
    210                 215                 220

Leu Glu Asp Pro Val Asp Ile Asp Arg Leu Glu Phe Ile His Leu His
225                 230                 235                 240

Lys Thr Ala Ala Leu Leu Glu Ala Ser Val Val Ile Gly Ala Val Val
                245                 250                 255

Gly Gly Gly Ser Asp Ser Glu Val Glu Arg Leu Arg Arg Tyr Ala Arg
            260                 265                 270

Cys Ile Gly Leu Leu Phe Gln Val Val Asp Asp Ile Leu Asp Val Thr
        275                 280                 285

Lys Ser Ser Gln Glu Leu Gly Lys Thr Ala Ala Lys Asp Leu Ala Ser
    290                 295                 300

Asn Lys Thr Thr Tyr Pro Lys Leu Leu Gly Leu Glu Lys Ser Arg Glu
```

```
            305                 310                 315                 320

Phe Ala Asp Glu Leu Leu Arg Asp Ala Lys Ser Gln Ile Glu Gly Phe
                        325                 330                 335

Asp Ser Leu Lys Ala Ala Pro Leu Leu His Leu Ala Asn Tyr Ile Ala
                        340                 345                 350

Tyr Arg Gln Asn
                    355

<210> SEQ ID NO 16
<211> LENGTH: 356
<212> TYPE: PRT
<213> ORGANISM: Phalaenopsis equestris

<400> SEQUENCE: 16

Met Ala Ser Phe Ala Thr Phe His Leu Ala Gly Ser His Pro Leu Arg
1               5                   10                  15

Ser Pro Phe Pro Thr Pro Thr Met Thr Val Leu Arg Pro Pro Ser Arg
                20                  25                  30

Ser Leu Ser Leu Ser Phe Pro Ser Leu Asn Ala Val Glu Thr Lys Ala
            35                  40                  45

Asp Pro Ser Val Ala Thr Thr Glu Phe Asp Phe Lys Gly Phe Leu Leu
        50                  55                  60

Lys Lys Ala Glu Ser Val Asn Arg Ala Leu Asp Leu Ala Ile Pro Leu
65                  70                  75                  80

Ile His Pro Lys Arg Ile His Glu Ala Met Arg Tyr Ser Leu Leu Ala
                85                  90                  95

Gly Gly Lys Arg Ile Arg Pro Val Leu Cys Ile Ala Ala Cys Glu Ile
                100                 105                 110

Val Gly Gly Asp Glu Ala Gln Ser Ile Pro Pro Ala Cys Ala Val Glu
            115                 120                 125

Met Ile His Thr Met Ser Leu Ile His Asp Asp Leu Pro Cys Met Asp
        130                 135                 140

Asp Asp Asp Leu Arg Arg Gly Lys Pro Ser Cys His Arg Ala Phe Gly
145                 150                 155                 160

Glu Ser Val Ala Val Leu Ala Gly Asp Ala Leu Leu Ala Leu Ala Phe
                165                 170                 175

Glu His Leu Val Asp Leu Arg Asn Tyr Pro Ser Ser Ile Ala Ile Ala
                180                 185                 190

Pro Ala Ile Leu Val Arg Ala Thr Ala Glu Leu Ala Arg Cys Ile Gly
            195                 200                 205

Thr Glu Gly Leu Val Ala Gly Gln Leu Leu Asp Met Glu Ser Thr Gly
        210                 215                 220

Leu Glu Asp Pro Val Asp Ile Asp Arg Leu Glu Phe Ile His Leu His
225                 230                 235                 240

Lys Thr Ala Ala Leu Leu Glu Ala Ser Val Val Ile Gly Ala Leu Val
                245                 250                 255

Gly Gly Gly Ser Asp Ser Glu Val Glu Arg Leu Arg Arg Tyr Ala Gln
                260                 265                 270

Cys Ile Gly Leu Leu Phe Gln Val Val Asp Asp Ile Leu Asp Val Thr
            275                 280                 285

Lys Ser Ser Gln Glu Leu Gly Lys Thr Ala Ala Lys Asp Leu Ala Ser
        290                 295                 300

Asn Lys Thr Thr Tyr Pro Lys Leu Leu Gly Leu Glu Lys Ser Arg Glu
305                 310                 315                 320
```

```
Phe Ala Asp Lys Leu Leu Arg Asp Ala Lys Ser Gln Ile Glu Gly Phe
                325                 330                 335

Asp Ser Ser Lys Ala Ala Pro Leu Leu His Leu Ala Asn Tyr Ile Ala
            340                 345                 350

Tyr Arg Gln Asn
        355

<210> SEQ ID NO 17
<211> LENGTH: 372
<212> TYPE: PRT
<213> ORGANISM: Arabidopsis

<400> SEQUENCE: 17

Met Glu Ala Gln Asn Ile Phe Leu Tyr Leu Leu Ile Val Phe Leu Ser
1               5                   10                  15

Leu His Phe Val Phe Thr Thr Leu Lys Gly Arg Leu Ser Pro Ala Asn
            20                  25                  30

Thr Arg Arg Leu Ile Arg Leu Leu His Ile Pro Ile Lys Ser Pro Val
        35                  40                  45

Ala Ala Ala Ile Phe Ala Arg Lys Asp Thr Arg Glu Phe Leu Asp Ser
    50                  55                  60

Ser Ile Lys Leu Val Asn Glu Glu Asp Asp Phe Gly Phe Ser Phe Asp
65                  70                  75                  80

Phe Lys Pro Tyr Met Ile Ser Lys Ala Glu Thr Ile Asn Arg Ala Leu
                85                  90                  95

Asp Glu Ala Ile Pro Leu Ile Glu Pro Leu Asn Ile His Lys Ala Met
            100                 105                 110

Arg Tyr Ala Ile Leu Ala Gly Gly Lys Arg Val Arg Pro Ile Leu Cys
        115                 120                 125

Leu Ala Ala Cys Glu Leu Val Gly Gly Glu Glu Arg Leu Ala Ile Gln
    130                 135                 140

Ala Ala Cys Ala Val Glu Met Ile His Thr Met Ser Leu Ile Lys Asp
145                 150                 155                 160

Asp Leu Pro Cys Met Asp Asn Asp Asp Leu Arg Arg Gly Lys Pro Thr
                165                 170                 175

Thr His Lys Val Phe Gly Glu Ser Val Ala Ile Leu Ser Gly Gly Ala
            180                 185                 190

Leu Leu Ala Leu Ala Phe Glu His Leu Thr Glu Ala Asp Val Ser Ser
        195                 200                 205

Lys Lys Met Val Arg Ala Val Lys Glu Leu Ala Lys Ser Ile Gly Thr
    210                 215                 220

Lys Gly Leu Val Ala Gly Gln Ala Lys Asp Leu Ser Ser Glu Gly Leu
225                 230                 235                 240

Glu Gln Asn Asp Val Gly Leu Glu Asp Leu Glu Tyr Ile His Val His
                245                 250                 255

Lys Thr Gly Ser Leu Leu Glu Ala Ser Ala Val Ile Gly Ala Val Ile
            260                 265                 270

Gly Gly Gly Thr Glu Lys Glu Ile Glu Lys Val Arg Asn Phe Ala Arg
        275                 280                 285

Cys Ile Gly Leu Leu Phe Gln Val Val Asp Asp Ile Leu Asp Glu Thr
    290                 295                 300

Lys Ser Ser Glu Glu Leu Gly Lys Thr Ala Gly Lys Asp Lys Val Ala
305                 310                 315                 320

Gly Lys Leu Thr Tyr Pro Lys Val Ile Gly Val Glu Lys Ser Lys Glu
                325                 330                 335
```

```
Phe Val Glu Lys Leu Lys Arg Asp Ala Arg Glu His Leu Gln Gly Phe
            340                 345                 350

Asp Ser Asp Lys Val Lys Pro Leu Ile Ala Leu Thr Asn Phe Ile Ala
            355                 360                 365

Asn Arg Asn His
        370

<210> SEQ ID NO 18
<211> LENGTH: 383
<212> TYPE: PRT
<213> ORGANISM: Abies grandis

<400> SEQUENCE: 18

Met Ala Tyr Ser Gly Met Ala Thr Ser Tyr His Gly Leu His Phe Met
1               5                   10                  15

Asn Ile Ala Thr Gln Glu Cys Asn Leu Lys Arg Leu Ser Ile Pro Ser
            20                  25                  30

Arg Arg Phe His Gly Val Ser Pro Ser Leu Trp Ala Ser Asn Gly Phe
        35                  40                  45

Gln Gly His Leu Lys Arg Glu Leu Ser Ala Asn Ser Phe Leu Val Ser
    50                  55                  60

Ser Ser Arg Tyr Ser Asn Thr Ile Ala Lys Phe Thr Asn Leu Pro Glu
65                  70                  75                  80

Lys Val Lys Glu Lys Val Ile Glu Phe Asp Phe Lys Glu Tyr Leu Arg
                85                  90                  95

Ser Lys Ala Met Ala Val Asn Glu Ala Leu Asp Arg Ala Val Pro Leu
            100                 105                 110

Arg Tyr Pro Glu Arg Ile His Glu Ala Met Arg Tyr Ser Leu Leu Ala
        115                 120                 125

Gly Gly Lys Arg Val Arg Pro Val Leu Cys Ile Ser Ala Cys Glu Leu
    130                 135                 140

Val Gly Gly Thr Glu Glu Val Ala Met Pro Thr Ala Cys Ala Met Glu
145                 150                 155                 160

Met Ile His Thr Met Ser Leu Ile His Asp Asp Leu Pro Cys Met Asp
                165                 170                 175

Asn Asp Asp Phe Arg Arg Gly Lys Pro Thr Asn His Lys Val Phe Gly
            180                 185                 190

Glu Gly Thr Ala Ile Leu Ala Gly Asp Ala Leu Leu Ser Phe Ala Phe
        195                 200                 205

Glu His Ile Ala Val Ser Thr Ser Lys Ser Val Gly Thr Asp Arg Ile
    210                 215                 220

Leu Arg Val Val Ser Glu Leu Gly Arg Thr Ile Gly Ser Gln Gly Leu
225                 230                 235                 240

Val Gly Gly Gln Val Ala Asp Ile Thr Ser Glu Gly Asp Ala Ser Val
                245                 250                 255

Asp Leu Asp Thr Leu Glu Trp Ile His Ile His Lys Thr Ala Val Leu
            260                 265                 270

Leu Glu Cys Ser Val Met Cys Gly Ala Ile Ile Ser Gly Ala Ser Asp
        275                 280                 285

Asn Glu Ile Glu Arg Ile Gln Arg Tyr Ala Arg Ser Val Gly Leu Leu
    290                 295                 300

Phe Gln Val Val Asp Asp Ile Leu Asp Val Thr Lys Ser Ser Lys Glu
305                 310                 315                 320

Leu Gly Lys Thr Ala Gly Lys Asp Leu Ile Ser Asp Lys Ala Thr Tyr
```

-continued

```
                325                 330                 335
Pro Lys Leu Met Gly Leu Glu Lys Ala Lys Gln Phe Ala Ser Asp Leu
                340                 345                 350
Leu Ile Arg Ala Lys Glu Asp Leu Ser Cys Phe Asp Pro Met Lys Ala
                355                 360                 365
Ala Pro Leu Leu Gly Leu Ala Asp Tyr Ile Ala Phe Arg Gln Asn
370                 375                 380

<210> SEQ ID NO 19
<211> LENGTH: 366
<212> TYPE: PRT
<213> ORGANISM: Oryza sativa

<400> SEQUENCE: 19

Met Ala Ala Phe His Pro Leu Ala Ala Ser Arg Val Arg Ile Ser Pro
1               5                   10                  15
Leu Ile Pro Ala Ala Met Ala Gly Thr Ala Gly Ala Ala Ala Ala Ala
                20                  25                  30
Ser Tyr Ala Gln His Arg Arg Phe Cys Ala Ile Val Ala Thr Ala
                35                  40                  45
Ala Ala Ser Pro Val Pro Ala Ala Ala Ala Ala Ala Thr Gly Phe
            50                  55                  60
Asp Phe Asn Ala Tyr Met Gly Glu Lys Ala Ala Val Asn Arg Ala
65                  70                  75                  80
Leu Asp Ala Ser Ile Pro Ala Asp Glu Pro Ala Ala Leu His Glu
                85                  90                  95
Ala Met Arg Tyr Ala Leu Leu Ala Gly Lys Arg Val Arg Pro Ala
                100                 105                 110
Leu Cys Leu Ala Ala Cys Ala Val Val Gly Gly Arg Glu Ala Trp Ala
                115                 120                 125
Met Pro Ala Ala Ala Val Glu Met Val His Thr Met Ser Leu Val
        130                 135                 140
His Asp Asp Leu Pro Cys Met Asp Asp Asp Leu Arg Arg Gly Lys
145                 150                 155                 160
Pro Thr Cys His Val Val Tyr Gly Glu Pro Ile Ala Val Leu Thr Gly
                165                 170                 175
Asp Ala Leu Leu Ser Leu Ser Phe His His Met Ala Arg Phe Asp Ser
                180                 185                 190
Tyr Pro Pro Asp Ile Asp Ala Asp Lys His Pro Ala Arg Val Val Arg
                195                 200                 205
Ala Ile Gly Glu Leu Ala Arg Cys Ile Gly Ser Gly Leu Val Ala
        210                 215                 220
Gly Gln Val Val Asp Leu Glu Met Thr Gly Ser Thr Glu Thr Val Pro
225                 230                 235                 240
Leu Glu Arg Leu Glu Tyr Ile His Leu His Lys Thr Ala Ala Leu Leu
                245                 250                 255
Glu Ala Ser Val Val Ile Gly Ala Ile Leu Gly Gly Ser Asp Glu
                260                 265                 270
Gln Ile Glu Ser Leu Arg Met Tyr Ala Arg Ser Ile Gly Leu Leu Phe
                275                 280                 285
Gln Val Val Asp Asp Ile Leu Asp Val Thr Lys Ser Ser Glu Glu Leu
        290                 295                 300
Gly Lys Thr Ala Gly Lys Asp Leu Ala Ser Asp Lys Thr Thr Tyr Pro
305                 310                 315                 320
```

```
Lys Leu Leu Gly Leu Glu Lys Ser Arg Glu Phe Ala Glu Lys Leu Leu
                325                 330                 335

Ser Asp Ala Arg Glu Gln Leu Ser Gly Phe Asp Gln Glu Thr Ala Ala
            340                 345                 350

Pro Leu Leu His Leu Ala Asn Tyr Ile Ala Tyr Arg Gln Asn
        355                 360                 365
```

<210> SEQ ID NO 20
<211> LENGTH: 371
<212> TYPE: PRT
<213> ORGANISM: Arabidopsis thaliana

<400> SEQUENCE: 20

```
Met Ala Ser Val Thr Leu Gly Ser Trp Ile Val Val His His Asn
1               5                   10                  15

His His His Pro Ser Ser Ile Leu Thr Lys Ser Arg Ser Arg Ser Cys
                20                  25                  30

Pro Ile Thr Leu Thr Lys Pro Ile Ser Phe Arg Ser Lys Arg Thr Val
            35                  40                  45

Ser Ser Ser Ser Ser Ile Val Ser Ser Val Val Thr Lys Glu Asp
    50                  55                  60

Asn Leu Arg Gln Ser Glu Pro Ser Ser Phe Asp Phe Met Ser Tyr Ile
65                  70                  75                  80

Ile Thr Lys Ala Glu Leu Val Asn Lys Ala Leu Asp Ser Ala Val Pro
                85                  90                  95

Leu Arg Glu Pro Leu Lys Ile His Glu Ala Met Arg Tyr Ser Leu Leu
            100                 105                 110

Ala Gly Gly Lys Arg Val Arg Pro Val Leu Cys Ile Ala Ala Cys Glu
        115                 120                 125

Leu Val Gly Gly Glu Glu Ser Thr Ala Met Pro Ala Ala Cys Ala Val
    130                 135                 140

Glu Met Ile His Thr Met Ser Leu Ile His Asp Asp Leu Pro Cys Met
145                 150                 155                 160

Asp Asn Asp Asp Leu Arg Arg Gly Lys Pro Thr Asn His Lys Val Phe
                165                 170                 175

Gly Glu Asp Val Ala Val Leu Ala Gly Asp Ala Leu Leu Ser Phe Ala
            180                 185                 190

Phe Glu His Leu Ala Ser Ala Thr Ser Ser Asp Val Val Ser Pro Val
        195                 200                 205

Arg Val Val Arg Ala Val Gly Glu Leu Ala Lys Ala Ile Gly Thr Glu
    210                 215                 220

Gly Leu Val Ala Gly Gln Val Val Asp Ile Ser Ser Glu Gly Leu Asp
225                 230                 235                 240

Leu Asn Asp Val Gly Leu Glu His Leu Glu Phe Ile His Leu His Lys
                245                 250                 255

Thr Ala Ala Leu Leu Glu Ala Ser Ala Val Leu Gly Ala Ile Val Gly
            260                 265                 270

Gly Gly Ser Asp Asp Glu Ile Glu Arg Leu Arg Lys Phe Ala Arg Cys
        275                 280                 285

Ile Gly Leu Leu Phe Gln Val Asp Asp Ile Leu Asp Val Thr Lys
    290                 295                 300

Ser Ser Lys Glu Leu Gly Lys Thr Ala Gly Lys Asp Leu Ile Ala Asp
305                 310                 315                 320

Lys Leu Thr Tyr Pro Lys Ile Met Gly Leu Glu Lys Ser Arg Glu Phe
                325                 330                 335
```

Ala Glu Lys Leu Asn Arg Glu Ala Arg Asp Gln Leu Leu Gly Phe Asp
            340                 345                 350

Ser Asp Lys Val Ala Pro Leu Leu Ala Leu Ala Asn Tyr Ile Ala Tyr
            355                 360                 365

Arg Gln Asn
    370

<210> SEQ ID NO 21
<211> LENGTH: 366
<212> TYPE: PRT
<213> ORGANISM: Sinapis Alba

<400> SEQUENCE: 21

Met Ala Ser Ser Val Thr Pro Leu Gly Ser Trp Val Leu Leu His His
1               5                   10                  15

His Pro Ser Thr Ile Leu Thr Gln Ser Arg Ser Arg Ser Pro Pro Ser
            20                  25                  30

Leu Ile Thr Leu Lys Pro Ile Ser Leu Thr Pro Lys Arg Thr Val Ser
            35                  40                  45

Ser Ser Ser Ser Ser Leu Ile Thr Lys Glu Asp Asn Asn Leu Lys
50                  55                  60

Ser Ser Ser Ser Phe Asp Phe Met Ser Tyr Ile Ile Arg Lys Ala
65                  70                  75                  80

Asp Ser Val Asn Lys Ala Leu Asp Ser Ala Val Pro Leu Arg Glu Pro
                85                  90                  95

Leu Lys Ile His Glu Ala Met Arg Tyr Ser Leu Leu Ala Gly Gly Lys
            100                 105                 110

Arg Val Arg Pro Val Leu Cys Ile Ala Ala Cys Glu Leu Val Gly Gly
            115                 120                 125

Glu Glu Ser Leu Ala Met Pro Ala Arg Cys Ala Val Glu Met Ile His
130                 135                 140

Thr Met Ser Leu Ile His Asp Asp Leu Pro Cys Met Asp Asn Asp Asp
145                 150                 155                 160

Leu Arg Arg Gly Lys Pro Thr Asn His Lys Val Tyr Gly Glu Asp Val
                165                 170                 175

Ala Val Leu Ala Gly Asp Ala Leu Leu Ser Phe Ala Phe Glu His Leu
            180                 185                 190

Ala Ser Ala Thr Ser Ser Glu Val Ser Pro Ala Arg Val Val Arg Ala
            195                 200                 205

Val Gly Glu Leu Ala Lys Ala Ile Gly Thr Glu Gly Leu Val Ala Gly
            210                 215                 220

Gln Val Val Asp Ile Ser Ser Glu Gly Leu Asp Leu Asn Asn Val Gly
225                 230                 235                 240

Leu Glu His Leu Lys Phe Ile His Leu His Lys Thr Ala Ala Leu Leu
                245                 250                 255

Glu Ala Ser Ala Val Leu Gly Gly Ile Ile Gly Gly Gly Ser Asp Glu
            260                 265                 270

Glu Ile Glu Arg Leu Arg Lys Phe Ala Arg Cys Ile Gly Leu Leu Phe
            275                 280                 285

Gln Val Val Asp Asp Ile Leu Asp Val Thr Lys Ser Ser Gln Glu Leu
            290                 295                 300

Gly Lys Thr Ala Gly Lys Asp Leu Ile Ala Asp Lys Leu Thr Tyr Pro
305                 310                 315                 320

Lys Leu Met Gly Leu Glu Lys Ser Arg Glu Phe Ala Glu Lys Leu Asn

```
                        325                 330                 335
Thr Glu Ala Arg Asp Gln Leu Leu Gly Phe Asp Ser Asp Lys Val Ala
                340                 345                 350
Pro Leu Leu Ala Leu Ala Asn Tyr Ile Ala Asn Arg Gln Asn
            355                 360                 365

<210> SEQ ID NO 22
<211> LENGTH: 350
<212> TYPE: PRT
<213> ORGANISM: Scoparia dulcis

<400> SEQUENCE: 22

Met Ser Leu Val Asn Pro Val Ser Thr Trp Pro Asn Pro Thr Arg Ser
1               5                   10                  15
Ser Val Phe Arg Pro Lys Pro Ala Ile Leu Asn Thr Thr His Leu Pro
            20                  25                  30
Ile Ser Phe Leu Phe Ala Gly Lys Pro Ile Ser Ala Val Leu Thr Lys
        35                  40                  45
Glu Tyr Ser His Gln Thr Ser Ser Thr Phe Asp Phe Lys Lys Tyr Met
    50                  55                  60
Leu Glu Lys Ala Ser Ser Val Asn Lys Ala Leu Glu Ser Ala Val Ser
65                  70                  75                  80
Leu Lys Glu Pro Leu Lys Ile His Glu Ser Met Arg Tyr Ser Leu Leu
                85                  90                  95
Ala Gly Gly Lys Arg Val Arg Pro Met Leu Cys Leu Ala Ala Cys Glu
            100                 105                 110
Leu Val Gly Gly His Pro Ser Thr Ala Met Pro Ala Ala Cys Ser Ile
        115                 120                 125
Glu Met Ile His Thr Met Ser Leu Met His Asp Asp Leu Pro Cys Met
    130                 135                 140
Asp Asn Asp His Leu Arg Arg Gly His Pro Thr Asn His Ile Val Phe
145                 150                 155                 160
Gly Glu Asp Val Ala Val Leu Ala Gly Asp Ala Leu Leu Ala Tyr Ser
                165                 170                 175
Phe Glu Tyr Leu Ala Thr Ala Thr Glu Gly Val Leu Pro Glu Arg Ile
            180                 185                 190
Val Arg Val Ile Ala Glu Leu Ala Lys Cys Ile Arg Ser Glu Gly Leu
        195                 200                 205
Leu Ala Gly Gln Val Val Asp Ile Cys Ser Glu Gly Val Ser Glu Ile
    210                 215                 220
Gly Leu Glu His Leu Glu Tyr Ile His Leu His Lys Thr Ala Ala Leu
225                 230                 235                 240
Leu Glu Gly Ser Val Val Leu Gly Ala Ile Leu Gly Gly Gly Asn Asp
                245                 250                 255
Glu Glu Val Glu Arg Leu Arg Lys Phe Ala Arg Cys Ile Gly Leu Leu
            260                 265                 270
Phe Gln Val Val Asp Asp Ile Leu Asp Val Thr Lys Thr Ser Val Glu
        275                 280                 285
Leu Gly Lys Thr Ala Gly Lys Asp Leu Val Ala Asp Lys Thr Thr Tyr
    290                 295                 300
Pro Lys Leu Ile Gly Ile Glu Lys Ser Arg Glu Phe Ala Glu Lys Leu
305                 310                 315                 320
Asn Arg Glu Ala Gln Glu Gln Leu Val Gly Phe Asp Ser Asp Lys Ala
                325                 330                 335
```

```
Ala Pro Leu Ile Ala Leu Ala Asn Tyr Ile Ala Tyr Arg Glu
            340                 345                 350

<210> SEQ ID NO 23
<211> LENGTH: 368
<212> TYPE: PRT
<213> ORGANISM: Croton sublyratus

<400> SEQUENCE: 23

Met Ser Ser Val Asn Leu Gly Ser Trp Val His Thr Ser Val Ile
1               5                   10                  15

Ser Gln Ala Thr Arg Ser Arg Ser Lys Ser Lys Pro Leu Ser Phe Ser
                20                  25                  30

Pro Val Ser Ile Pro Leu Phe Tyr Arg Asn Ser Lys Arg Ser Val Ser
            35                  40                  45

Tyr Val Ser Ala Ile Val Thr Lys Asp Glu Thr Ile Gln Glu Glu
    50                  55                  60

Gln Asn Lys Asn Ser Ser Ser Leu Gly Phe Asp Phe Lys Ser Tyr
65                  70                  75                  80

Met Val Gln Lys Ala Ser Ala Ile Asn Gln Ala Leu Glu Ala Val
                85                  90                  95

Ser Leu Arg Glu Pro Leu Lys Ile His Glu Ser Met Arg Tyr Ser Leu
                100                 105                 110

Leu Ala Gly Gly Lys Arg Val Arg Pro Ala Leu Cys Leu Ala Ala Cys
            115                 120                 125

Glu Leu Val Gly Gly Asp Glu Ser Met Ala Met Pro Ala Ala Cys Ala
130                 135                 140

Val Glu Met Ile His Thr Met Ser Leu Ile His Asp Asp Leu Pro Cys
145                 150                 155                 160

Met Asp Asn Asp Asp Leu Arg Arg Gly Lys Pro Thr Asn His Ile Val
                165                 170                 175

Phe Gly Glu Asn Val Ala Val Leu Ala Gly Asp Ala Leu Leu Ala Phe
            180                 185                 190

Ala Phe Glu His Ile Ala Val Ser Thr Leu Asn Val Ser Pro Val Arg
        195                 200                 205

Ile Val Arg Gly Val Gly Glu Leu Ala Lys Ala Ile Gly Ala Glu Gly
    210                 215                 220

Leu Val Ala Gly Gln Val Val Asp Ile Cys Ser Glu Gly Leu Ser Glu
225                 230                 235                 240

Val Asp Leu Glu Lys Leu Glu Phe Ile His Ile His Lys Thr Ala Lys
                245                 250                 255

Leu Leu Glu Gly Ala Val Val Leu Gly Ala Ile Met Gly Gly Gly Thr
            260                 265                 270

Asp Glu Glu Val Glu Lys Leu Arg Lys Tyr Ala Arg Asp Ile Gly Leu
        275                 280                 285

Leu Phe Gln Val Val Asp Asp Ile Leu Asp Val Thr Lys Ser Ser Gln
    290                 295                 300

Glu Leu Gly Lys Thr Ala Gly Lys Asp Leu Val Ala Asp Lys Val Thr
305                 310                 315                 320

Tyr Pro Lys Leu Met Gly Ile Glu Lys Ser Arg Glu Phe Ala Glu Lys
                325                 330                 335

Leu Asn Lys Glu Ala Gln Glu Gln Leu Ala Gly Phe Asp Pro Glu Lys
            340                 345                 350

Ala Ala Pro Leu Ile Ala Leu Ala Asn Tyr Ile Ala Tyr Arg Gln Asn
        355                 360                 365
```

<210> SEQ ID NO 24
<211> LENGTH: 372
<212> TYPE: PRT
<213> ORGANISM: Medicago

<400> SEQUENCE: 24

```
Met Ser Ala Val Asn Leu Asn Thr Trp Thr His Ser Asn Phe Met Cys
1               5                   10                  15

Asn Gln Val Thr Thr Thr Ala Thr Thr Arg Ser Arg Ser Arg Ile Pro
            20                  25                  30

Ser Phe Tyr Phe Thr Lys Ile Pro Ile Ser Val Ser Pro Ile Lys Pro
        35                  40                  45

Ser Lys Pro Asn Ser Ser Ser Phe Ser Phe Ser Val Ser Ser Leu Leu
    50                  55                  60

Thr Lys Gln Glu Pro Ile Glu Ala Glu Glu Gln Asn Pro Ile Phe Asn
65                  70                  75                  80

Phe Lys Ser Tyr Met Ile Glu Lys Ala Thr Arg Val Asn Lys Ala Leu
                85                  90                  95

Asp Asp Ala Val Ser Leu Arg Glu Pro Leu Lys Val His Glu Ala Met
            100                 105                 110

Arg Tyr Ser Leu Leu Ala Gly Gly Lys Arg Val Arg Pro Val Leu Cys
        115                 120                 125

Leu Ala Ala Cys Glu Leu Val Gly Gly Thr Glu Pro Met Ala Met Pro
    130                 135                 140

Ala Ala Cys Ala Val Glu Met Ile His Thr Met Ser Leu Ile His Asp
145                 150                 155                 160

Asp Leu Pro Cys Met Asp Asn Asp Asp Leu Arg Arg Gly Lys Pro Thr
                165                 170                 175

Asn His Lys Val Phe Gly Glu Asp Val Ala Val Leu Ala Gly Asp Ala
            180                 185                 190

Leu Leu Ala Phe Ala Phe Glu His Ile Ala Val Ser Thr Val Asp Val
        195                 200                 205

Ser Pro Ala Arg Ile Val Arg Ala Ile Gly Glu Leu Ala Lys Ser Ile
    210                 215                 220

Gly Ser Glu Gly Leu Val Ala Gly Gln Val Val Asp Ile Asn Ser Glu
225                 230                 235                 240

Gly Leu Ser Asp Val Gly Leu Glu Arg Leu Glu Phe Ile His Leu His
                245                 250                 255

Lys Thr Ala Ala Leu Leu Glu Gly Ala Val Val Leu Gly Ala Ile Leu
            260                 265                 270

Gly Gly Gly Ser Asp Glu Asp Val Glu Lys Leu Arg Lys Phe Ala Thr
        275                 280                 285

Tyr Ile Gly Leu Leu Phe Gln Val Val Asp Asp Ile Leu Asp Val Thr
    290                 295                 300

Lys Ser Ser Gln Glu Leu Gly Lys Thr Ala Gly Lys Asp Leu Val Ala
305                 310                 315                 320

Asp Lys Val Thr Tyr Pro Lys Leu Leu Gly Ile Glu Lys Ser Lys Glu
                325                 330                 335

Phe Ala Glu Lys Leu Asn Arg Asp Ala Gln Glu Gln Leu Ser Gly Phe
            340                 345                 350

Asp Leu Asn Lys Ser Ala Pro Leu Ile Ala Leu Ala Asn Tyr Ile Ala
        355                 360                 365

Tyr Arg Gln Asn
```

```
<210> SEQ ID NO 25
<211> LENGTH: 308
<212> TYPE: PRT
<213> ORGANISM: Vitis vinifera

<400> SEQUENCE: 25

Met Val Arg Gly Gly Asp Thr Pro Glu Glu Lys Pro Ala Phe Asn
1               5                   10                  15

Phe Asn Ala Tyr Ile Leu Asp Lys Ala Asn Ser Val Asn Lys Ala Leu
            20                  25                  30

Asp Asp Ala Val Pro Ile Arg Glu Pro Val Lys Val His Glu Ser Met
        35                  40                  45

Arg Tyr Ser Leu Leu Ala Gly Gly Lys Arg Val Arg Pro Val Leu Cys
    50                  55                  60

Ile Ala Ala Cys Glu Leu Val Gly Gly Asp Glu Ala Thr Ala Met Pro
65                  70                  75                  80

Ala Ala Cys Ala Val Glu Met Ile His Thr Met Ser Leu Met His Asp
                85                  90                  95

Asp Leu Pro Cys Met Asp Asn Asp Asp Leu Arg Arg Gly Lys Pro Thr
            100                 105                 110

Asn His Lys Val Phe Gly Glu Asn Val Ala Ile Leu Ala Gly Asp Ala
        115                 120                 125

Leu Leu Ala Phe Ala Phe Glu His Met Ala Thr Ala Thr Val Gly Val
    130                 135                 140

Pro Pro Gly Trp Ile Val Arg Ala Val Gly Glu Leu Ala Lys Ser Ile
145                 150                 155                 160

Gly Ser Glu Gly Leu Val Ala Gly Gln Val Val Asp Ile Cys Ser Glu
                165                 170                 175

Gly Leu Lys Asp Val Gly Leu Glu His Leu Glu Tyr Ile His Val His
            180                 185                 190

Lys Thr Ala Ala Leu Leu Glu Gly Ala Val Val Leu Gly Ala Ile Leu
        195                 200                 205

Gly Gly Gly Ser Asn Glu Glu Ile Glu Lys Leu Arg Lys Phe Ala Arg
    210                 215                 220

Cys Ile Gly Leu Leu Phe Gln Val Val Asp Asp Ile Leu Asp Val Thr
225                 230                 235                 240

Lys Ser Ser Gln Glu Leu Gly Lys Thr Ala Gly Lys Asp Leu Val Ala
                245                 250                 255

Asp Lys Leu Thr Tyr Pro Lys Leu Leu Gly Ile Glu Lys Ser Arg Glu
            260                 265                 270

Leu Ala Glu Gln Leu Asn Lys Asp Ala Lys Gln Leu Ser Gly Phe
        275                 280                 285

Asp Pro Asp Lys Ala Ala Pro Leu Ile Ala Leu Ser Asn Tyr Ile Ala
    290                 295                 300

Tyr Arg Gln Asn
305

<210> SEQ ID NO 26
<211> LENGTH: 369
<212> TYPE: PRT
<213> ORGANISM: Capsicum annuum

<400> SEQUENCE: 26

Met Arg Ser Met Asn Leu Val Asp Leu Trp Ala Gln Gln Ala Cys Leu
```

```
  1               5                  10                 15
Val Phe Asn Gln Thr Leu Ser Tyr Lys Ser Phe Asn Gly Phe Met Lys
            20                  25                 30

Ile Pro Leu Lys Asn Ser Lys Ile Asn Pro Lys Leu Asn Lys Lys Arg
            35                  40                 45

Pro Phe Ser Pro Leu Thr Val Ser Ala Ile Ala Thr Thr Lys Glu Asp
50                       55                 60

Glu Arg Ile Glu Ala Ala Gln Thr Glu Glu Pro Phe Asn Phe Lys Ile
65                  70                  75                 80

Tyr Val Thr Glu Lys Ala Ile Ser Val Asn Lys Ala Leu Asp Glu Ala
                85                  90                  95

Ile Ile Val Lys Glu Pro His Val Ile His Glu Ala Met Arg Tyr Ser
                100                 105                 110

Leu Leu Ala Gly Gly Lys Arg Val Arg Pro Met Leu Cys Leu Ala Ala
                115                 120                 125

Cys Glu Leu Val Gly Gly Asn Gln Glu Asn Ala Met Ala Ala Ala Cys
    130                 135                 140

Ala Val Glu Met Ile His Thr Met Ser Leu Ile His Asp Asp Leu Pro
145                 150                 155                 160

Cys Met Asp Asn Asp Asp Leu Arg Arg Gly Lys Pro Thr Asn His Lys
                165                 170                 175

Ile Tyr Gly Glu Asp Val Ala Val Leu Ala Gly Asp Ser Leu Leu Ala
                180                 185                 190

Phe Ala Phe Glu His Ile Val Asn Ser Thr Ala Gly Val Thr Pro Ser
            195                 200                 205

Arg Ile Val Gly Ala Val Ala Glu Leu Ala Lys Ser Ile Gly Thr Glu
    210                 215                 220

Gly Leu Val Ala Gly Gln Val Ala Asp Ile Lys Cys Thr Gly Asn Ala
225                 230                 235                 240

Ser Val Ser Leu Glu Thr Leu Glu Phe Ile His Val His Lys Thr Ala
                245                 250                 255

Ala Leu Leu Glu Ser Ser Val Val Leu Gly Ala Ile Leu Gly Gly Gly
                260                 265                 270

Thr Asn Val Glu Val Glu Lys Leu Arg Arg Phe Ala Arg Cys Ile Gly
                275                 280                 285

Leu Leu Phe Gln Val Val Asp Asp Ile Leu Asp Val Thr Lys Ser Ser
            290                 295                 300

Glu Glu Leu Gly Lys Thr Ala Gly Lys Asp Leu Val Val Asp Lys Thr
305                 310                 315                 320

Thr Tyr Pro Lys Leu Leu Gly Leu Glu Lys Ala Lys Glu Phe Ala Ala
                325                 330                 335

Glu Leu Asn Arg Glu Ala Lys Gln Gln Leu Glu Gly Phe Asp Ser Arg
                340                 345                 350

Lys Ala Ala Pro Leu Ile Ala Leu Ala Asp Tyr Ile Ala Tyr Arg Asp
                355                 360                 365

Asn
```

<210> SEQ ID NO 27
<211> LENGTH: 367
<212> TYPE: PRT
<213> ORGANISM: Gentiana lutea

<400> SEQUENCE: 27

Met Val Asp Ser Trp Val Val Gln Ser His Ser Val Phe His Thr Pro

```
  1               5                  10                 15
Ile Ser Leu Phe Arg Ser Phe Leu Gly Phe Leu Cys Lys Pro Met Asn
             20                 25                 30

Tyr Asn Lys Ile Gly Ser Asn Leu Ile Glu Lys Lys Leu Ile Ser
             35                 40                 45

Ser Phe Ser Val Ala Ser Leu Ile Thr Lys Glu Glu Ala Met Gly
             50                 55                 60

Gly Pro Lys Ala Ser Asn Tyr Phe Asp Phe Lys Ala Tyr Leu Ile Glu
 65              70                 75                 80

Lys Ala Asn Lys Val Asn Glu Ala Leu Asp Gln Ala Val Ser Val Lys
                 85                 90                 95

Asn Pro Pro Met Ile His Glu Ala Met Arg Tyr Ser Leu Leu Ala Gly
                100                105                110

Gly Lys Arg Val Arg Pro Ile Leu Cys Ile Ala Ala Cys Glu Leu Val
                115                120                125

Gly Gly Glu Glu Ser Asn Ser Val Pro Ala Ala Cys Ala Val Glu Met
                130                135                140

Ile His Thr Met Ser Leu Ile His Asp Asp Leu Pro Cys Tyr Gly Gln
145                150                155                160

Arg Asp Leu Arg Arg Gly Lys Ala His Glu Thr Thr Lys Ser Ser Cys
                165                170                175

Glu Asp Val Ala Val Leu Ala Gly Asp Ser Leu Leu Ala Phe Ser Phe
                180                185                190

Glu Tyr Ile Ala Thr Ala Thr Lys Asn Val Ser Pro Ala Lys Asn Phe
                195                200                205

Ser Arg Ser Arg Arg Ile Ser Lys Ser Ile Gly Thr Glu Gly Leu Val
210                215                220

Ala Gly Gln Val Ala Asp Phe Val Ile Asn Gly Glu Asn Gln Met Phe
225                230                235                240

Gly Leu Asp Gln Leu Glu Phe Ile His Ile His Lys Thr Ala Ala Leu
                245                250                255

Leu Glu Ala Ala Val Val Leu Gly Ala Ile Leu Gly Gly Gly Asn Pro
                260                265                270

Glu Glu Val Glu Lys Leu Arg Arg Phe Ala Arg Cys Ile Gly Leu Leu
                275                280                285

Phe Gln Val Val Asp Asp Ile Leu Asp Val Thr Lys Ser Ser Glu Glu
                290                295                300

Leu Gly Lys Thr Ala Gly Lys Arg Ser Cys Gly Gly Lys Thr Thr Tyr
305                310                315                320

Pro Lys Leu Met Gly Leu Asp Gly Ala Arg Glu Phe Ala Asp Lys Leu
                325                330                335

Asn Lys Asp Ala Lys Asn Gln Leu Ser Glu Phe Asp Arg Glu Lys Ala
                340                345                350

Ala Pro Leu Leu Ala Leu Ala Asp Tyr Ile Ala Tyr Arg Gln Asn
                355                360                365

<210> SEQ ID NO 28
<211> LENGTH: 356
<212> TYPE: PRT
<213> ORGANISM: Helianthus annuus

<400> SEQUENCE: 28

Met Arg Pro Met Ser Leu Val His Ser Cys Ser Ile Phe Thr Gly Ser
 1               5                  10                 15
```

-continued

```
Ser Phe Ile Lys Thr Thr Pro Ile Asn Asn Lys Pro Thr Phe Lys Ile
            20                  25                  30

His Gln Arg Pro Thr Ile Arg Ser Thr Ile Ser Ala Ala Ile Val Glu
        35                  40                  45

Glu Glu Val Val Glu Leu Gln Gln Lys Pro Lys Pro Thr Phe Asn Phe
    50                  55                  60

Asn Ala Tyr Met Leu Gly Lys Gly Asn Ser Val His Lys Ala Leu Asp
65                  70                  75                  80

Glu Ser Ile Met Ile Lys Asn Pro Pro Thr Ile His Glu Ala Met Arg
                85                  90                  95

Tyr Ser Leu Leu Ala Gly Gly Lys Arg Val Arg Pro Ile Leu Cys Ile
            100                 105                 110

Ala Ala Cys Glu Leu Val Gly Gly Glu Glu Ala Thr Ala Met Pro Ala
        115                 120                 125

Ala Cys Ala Val Glu Met Ile His Thr Met Ser Leu Ile His Asp Asp
    130                 135                 140

Leu Pro Cys Met Asp Asn Asp Asp Phe Arg Arg Gly Lys Pro Thr Asn
145                 150                 155                 160

His Lys Val Tyr Gly Glu Asp Val Ala Val Leu Ala Gly Asp Ser Leu
                165                 170                 175

Leu Ala Phe Ala Phe Glu Tyr Val Ser Ser Arg Thr Glu Gly Ala Ser
            180                 185                 190

Pro Ala Arg Val Leu Ala Ala Ile Gly Glu Leu Ala Lys Ser Ile Gly
        195                 200                 205

Thr Glu Gly Leu Val Ala Gly Gln Val Val Asp Ile Ala Ser Thr Gly
    210                 215                 220

Gly Gln Asp Ile Gly Leu Asp Gln Leu Glu Phe Ile His Ile His Lys
225                 230                 235                 240

Thr Ala Ala Leu Leu Glu Ala Ser Val Val Leu Gly Ala Ile Leu Gly
                245                 250                 255

Gly Gly Ser Asp Ala Gln Val Glu Lys Leu Arg Thr Phe Ala Arg Cys
            260                 265                 270

Ile Gly Leu Leu Phe Gln Val Val Asp Asp Ile Leu Asp Val Thr Lys
        275                 280                 285

Ser Ser Glu Glu Leu Gly Lys Thr Ala Gly Lys Asp Leu Leu Val Asp
    290                 295                 300

Lys Thr Thr Tyr Pro Lys Leu Leu Gly Leu Asp Lys Ser Arg Gln Phe
305                 310                 315                 320

Ala Glu Glu Leu Leu Ala Glu Ala Lys Gln Gln Leu Glu Glu Phe Glu
                325                 330                 335

Ser Gln Ala Ala Val Ala Pro Leu Leu Ala Leu Ala Glu Tyr Ile Ala
            340                 345                 350

Tyr Arg Gln Asn
            355
```

GENE, PROTEIN, PROTEIN COMPLEX AND METHOD FOR IMPROVING AROMA PRODUCTION IN A PLANT

BACKGROUND OF THE INVENTION

1. Field of the Invention

The invention relates to a gene for improving aroma production in a plant, and more particularly to a gene, protein, protein complex and method for improving aroma production in a plant.

2. Description of the Related Art

Flowers are unique organs that advertise their attractiveness in form, color and fragrance for insects, birds and mammals to assure pollination. Orchidaceae is one of the largest monocotyledon families, containing more than 25,000 species. In orchids, large quantities of pollen in masses are spread by animals (bees, moths, flies and birds), and the floral scents serve as attractants for species-specific pollinators. These pollinators play an important role in orchid floral diversification advantageous to the evolution of an obviously successful family. However, the biochemistry of fragrance production and the mechanisms regulating its emission in orchids remains sketchy.

To date, no simple, efficient, and reliable culture methods for scented orchids have been developed. Although the sympatric speciation of orchids is linked to differences in their floral odors, the large genome size, long life cycle and regeneration time and inefficient transformation system render the orchid scent biology difficult to explore. Furthermore, several scent and scentless species are cross-incompatible, which leads to the difficulty of producing scented offspring via traditional breeding. In some successful cases of cross-breeding, the offspring have diluted scent or even totally expel the scent-producing ability. Thus, to increase crop quality, the molecular breeding of scent species by introducing key enzymes regulating scent production to species/cultivars already with good characters is of interest.

Terpenoids belong to a large family of plant secondary metabolites, and their corresponding alcohols possess useful properties such as fragrance, flavor, insecticidal properties and characteristics that make them useful as pharmaceutical agents. In addition, primary metabolites like abscisic acid, carotenoids, chlorophyll, gibberellins, quinine electron carriers and steroids are also terpene-derived (van Schie et al., 2007, Plant J, 52, 752-762). Monoterpens formed from geranyl diphosphate (GDP, $C_{10}$, is synthesized from dimethylallyl diphosphate (DMADP, $C_5$) and isopentenyl diphosphate (IDP, $C_5$) by GDP synthase (GDPS). IDP and DMADP are used by prenyltransferases to catalyze the synthesis of the general terpene backbones. GDPS is a member of the short-chain trans-prenyltransferase family, and it also includes farnesyl diphosphate synthase (FDPS) and geranylgeranyl diphosphate synthase (GGDPS), which synthesize farnesyl diphosphate (FDP, $C_{15}$) and geranylgeranyl diphosphate (GGDP, C20), respectively (Ogura and Koyama, 1998, Chem. Rev., 98, 1263-1276; Reiling et al., 2004, Biotechnol Bioeng, 87, 200-212). These enzymes provide the acyclic branch-point intermediates for isoprenoid biosynthesis and control the flux into various terpenoid products. However, regulation and sharing of precursor pools are only starting to be explored.

The distribution of GDPS appears to be limited within nature. It has been described in the plants *Mentha piperita* (Burke et al., 1999, Proc Natl Acad Sci USA, 96, 13062-13067), *Arabidopsis thaliana* (Bouvier et al., 2000, Plant J, 24, 241-252), *Abies grandis* (Burke and Croteau, 2002, Arch Biochem Biophys, 405, 130-136), *Antirrhinum majus, Clarkia breweri* (Tholl et al., 2004, Plant Cell, 16, 977-992), *Lycopersicon esculentum* (van Schie et al., 2007, Plant J, 52, 752-762) and *Phalaenopsis bellina* (Hsiao et al., 2008, Plant J, 55, 719-733). GDPSs are either homomeric or heteromeric; the *A. grandis, Arabidopsis* and tomato GDPS, which contain the Asp-rich motifs and presume function as homodimers (Bohlmann et al., 2000, Arch Biochem Biophys, 375, 261-269; Burke and Croteau, 2002, Arch Biochem Biophys, 405, 130-136; van Schie et al., 2007, Plant J, 52, 752-762). The *M. piperita, A. majus*, and *C. breweri* GDPSs comprise heterodimers of a small (Mentha_SSU, Antirrhinum_SSU and Clarkia_SSU) and a large subunit (Mentha_LSU and Antirrhinum_LSU), which share only 22-38% identity with homomeric angiosperm GDPSs or GGDPSs (Burke et al., 2004, Arch Biochem Biophys, 422, 52-60; Tholl et al., 2004, Plant Cell, 16, 977-992). Notably, the small subunit from these plants lacks the Asp-rich motifs and is inactive per se (Tholl et al., 2004, Plant Cell, 16, 977-992). It appears to control the length of the chain synthesized by the catalytic large subunit, because interaction of the small subunit with GGDPS results in the conversion of functional GGDPS into GDPS (Tholl et al., 2004, Plant Cell, 16, 977-992). Meanwhile, the GDPS large subunit shares high amino acid sequence identity with GGDPS from plants (50%-75%), but the Mentha_LSU and Antirrhinum_LSU per se forms an active GGDPS enzyme that produces GGDP (Tholl et al., 2004, Plant Cell, 16, 977-992). Thus, the frequency of occurrence of the GDPS large subunit in plants has remained an open question.

Previously, floral scents in *P. bellina* (Orchidaceae, monocot) are demonstrated to be rich in the monoterpenes, geraniol and linalool and their derivatives (Hsiao et al., 2006, BMC Plant Biol, 6, 14). Identification a dual-function GDPS that lacks the Asp-rich motifs normally required for scent production but contains instead a glutamate-rich (Glu-rich) motif and is able to form a homodimer. Recent researches showed that GDPS small subunit from *M. piperita, A. majus*, and *C. breweri* is capable of modifying the chain length specificity of its catalytic partner and can bind to a variety of bona fide GDPS_LSU and GGPPS enzymes (Burke and Croteau, 2002, J Biol Chem, 277, 3141-3149; Tholl et al., 2004, Plant Cell, 16, 977-992). None of the previous studies of heterodimer GDPS have been performed in plant of monocots. It is curious that whether or not the heterodimer GDPS exists in orchid flower.

SUMMARY OF THE INVENTION

The present invention provides the isolation and heterologous expression of a PbGDPS large subunit, whose sequence was similar to plant GGDPS. The mode of action either as a homodimer or as a heterodimer with PbGDPS small subunit in *P. bellina* flower is also illustrated.

One subject of the invention is to provide an isolated nucleic acid molecule, which nucleic acid molecule is selected form the group consisting of:
  (a) a nucleic acid molecule, PbGDPS_LSU, comprising a nucleotide sequence of SEQ ID NO: 1;
  (b) a nucleic acid molecule encoding a polypeptide comprising an amino acid sequence of SEQ ID NO: 2;
  (c) a nucleic acid molecule encoding a polypeptide comprising an amino acid sequence of SEQ ID NO: 2 with one or more of the amino acids have been modified by a deletion, an insertion and/or a substitution, wherein the polypeptide has a geranyl diphosphate synthase activity and/or farnesyl diphosphate synthase activity;

(d) a nucleic acid molecule encoding a polypeptide comprising an amino acid sequence with at least 85% similarity to SEQ ID NO: 2, wherein the polypeptide has a geranyl diphosphate synthase activity and/or farnesyl diphosphate synthase activity;

(e) a nucleic acid molecule complementary to any one of the nucleic acid molecules as defined in (a), (b), (c) and (d); and (f) a nucleic acid molecule hybridizes under stringent hybridization conditions to any one of the nucleic acid molecules as defined in (a), (b), (c), (d) and (e).

Another subject of the invention is to provide a cell comprising the isolated nucleic acid molecule mentioned above.

Still another subject of the invention is to provide a transgenic plant comprising the nucleic acid molecule mentioned above.

Still another subject of the invention is to provide a protein, which protein comprises a polypeptide selected from the group consisting of:

(a) a polypeptide, PbGDPS_LSU, comprising an amino acid sequence of SEQ ID NO: 2;

(b) a polypeptide comprising an amino acid sequence of SEQ ID NO: 2 with one or more of the amino acids have been modified by a deletion, an insertion and/or a substitution, wherein the polypeptide has a geranyl diphosphate synthase activity and/or farnesyl diphosphate synthase activity; and (c) a polypeptide comprising an amino acid sequence with at least 85% similarity to SEQ ID NO: 2, wherein the polypeptide has a geranyl diphosphate synthase activity and/or farnesyl diphosphate synthase activity.

Still another subject of the invention is to provide a method for improving the production of aroma in a plant, which comprises increasing the expression of the protein mentioned above.

Still another subject of the invention is to provide a protein complex comprising the protein mentioned and a functional geranyl diphosphate synthase small subunit, wherein the functional geranyl diphosphate synthase small subunit is selected from the group consisting of:

(a) a polypeptide, PbGDPS_SSU, comprising an amino acid sequence of SEQ ID NO: 4;

(b) a polypeptide comprising an amino acid sequence of SEQ ID NO: 4 with one or more of the amino acids have been modified by a deletion, an insertion and/or a substitution, wherein the polypeptide has a geranyl diphosphate synthase activity and/or farnesyl diphosphate synthase and/or farnesyl diphosphate synthase activity; and (c) a polypeptide comprising an amino acid sequence with at least 40% similarity to SEQ ID NO: 4, wherein the polypeptide has a geranyl diphosphate synthase activity and/or farnesyl diphosphate synthase and/or farnesyl diphosphate synthase activity.

Still another subject of the invention is to provide a method for improving aroma production in a plant, which comprises increasing the expression of the protein complex mentioned above.

BRIEF DESCRIPTION OF THE DRAWINGS

FIGS. 1A, 1B and 1C illustrate alignment of amino acid sequences of GDPS-a family and GGDPS in *M. piperita* GDPS large subunit (GDPS_Mentha_LSU, SEQ ID NO: 14), AF182828; *A. majus* GDPS large subunit (GDPS_Antirrhinum_LSU, SEQ ID NO: 13), AY534687; *Abies grandis* GDPS (SEQ ID NOs: 11 and 12), AF513111, AF513112, AF513112; *Arabidopsis* GGDPS1 (SEQ ID NO: 20), NP_195399; *Capsicum annuum* GGDPS (SEQ ID NO: 26), X80267; *A. grandis* GGDPS (SEQ ID NO: 18), AF425235; *Oryza sativa* GGDPS (SEQ ID NO: 19), CM000132.1, *Croton sublyratus* GGDPS (SEQ ID NO: 23), AB034249.1, *Gentiana lutea* GGDPS (SEQ ID NO: 27), AB028667.1; *V. vinifera* GGDPS (SEQ ID NO: 25), AM438997.2; *Scoparia dulcis* GGDPS (SEQ ID NO: 22), AB034250.1; *Helianthus annuus* GGDPS (SEQ ID NO: 28), AF020041.1; *Sinapis Alba* GGDPS (SEQ ID NO: 21), 2J1P_A. The conserved aspartate-rich motifs (DDXXD) are shown in box. Dashes indicate gaps inserted for optimal alignment.

DETAILED DESCRIPTION OF THE INVENTION

Figure 2:
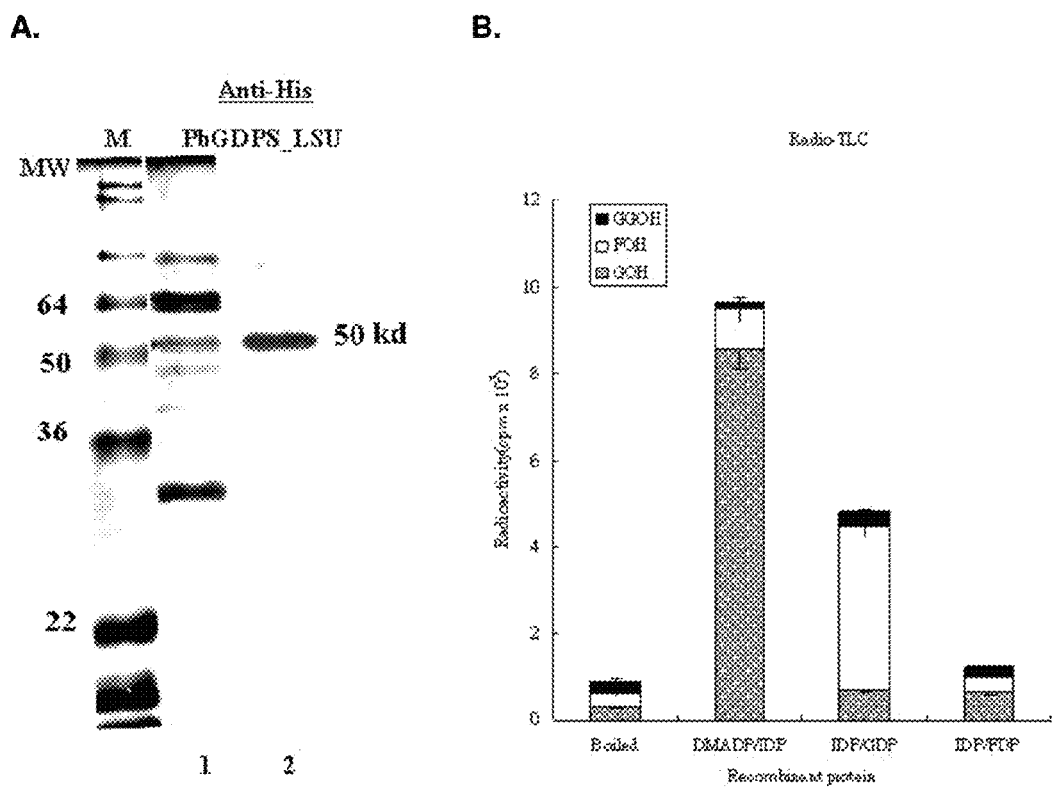
FIG. 2 illustrates enzyme activity of PbGDPS_LSU. (A) Expression of recombinant PbGDPS_LSU. Partial purified His-tagged PbGDPS_LSU from *E. coli* (lane 1), and western blot with anti-His tag antibody (lane 2). Molecular mass markers are indicated on the left margin. (B) Quantification of the products derived by enzymatic hydrolysis of prenyl diphosphate products shown on radioactive thin-layer chromatography (TLC) analysis. Prenyltransferase activity of purified recombinant PbGDPS_LSU protein (100 μg) was using various prenyldiphosphates with different chain lengths as substrates. Following incubation of boiled protein and PbGDPS_LSU recombinant protein with the [4-$^{14}$C]IPP, DMADP, GDP, and FDP, the reaction products were dephosphorylated. The experiment was repeated for three times independently.

One subject of the invention is to provide an isolated nucleic acid molecule, which nucleic acid molecule is selected form the group consisting of:
(a) a nucleic acid molecule, PbGDPS_LSU, comprising a nucleotide sequence of SEQ ID NO: 1;
(b) a nucleic acid molecule encoding a polypeptide comprising an amino acid sequence of SEQ ID NO: 2;
(c) a nucleic acid molecule encoding a polypeptide comprising an amino acid sequence of SEQ ID NO: 2 with one or more of the amino acids have been modified by a deletion, an insertion and/or a substitution, wherein the polypeptide has a geranyl diphosphate synthase activity and/or farnesyl diphosphate synthase activity;
(d) a nucleic acid molecule encoding a polypeptide comprising an amino acid sequence with at least 85% similarity to SEQ ID NO: 2, wherein the polypeptide has a geranyl diphosphate synthase activity and/or farnesyl diphosphate synthase activity;
(e) a nucleic acid molecule complementary to any one of the nucleic acid molecules as defined in (a), (b), (c) and (d); and
(f) a nucleic acid molecule hybridizes under stringent hybridization conditions to any one of the nucleic acid molecules as defined in (a), (b), (c), (d) and (e).

As utilized in accordance with the present disclosure, the following terms, unless otherwise indicated, shall be understood to have the following meanings:

The term "isolated nucleic acid molecule" as used herein refers to a nucleic acid molecule that (1) is not associated with all or a portion of a nucleic acid molecule in which the isolated nucleic acid molecule is found in nature, (2) is linked to a nucleic acid molecule to which it is not linked in nature, or (3) does not occur in nature as part of a larger sequence. Preferably, the isolated nucleic acid molecule is a polynucleotide. Examples of the isolated nucleic acid molecule are genomic DNA, mRNA, cDNA, or synthetic origin or some combination thereof, which by virtue of its origin the isolated nucleic acid molecule. The isolated nucleic acid molecule according to the invention preferably comprises a guide sequence, a coding region, an exon or an intron. An additional nucleic acid that does not affect the function of the isolated nucleic acid molecule is preferably contained. For example, several numbers of nucleic acids are contained in the 5' and 3' untranscribed regions.

The term "polynucleotide" as referred to herein means single-stranded or double-stranded nucleic acid polymers of at least 10 bases in length. In certain embodiments, the nucleotides comprising the polynucleotide can be ribonucleotides or deoxyribonucleotides or a modified form of either type of nucleotide. Said modifications include base modifications such as bromuridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single and double stranded forms of DNA.

In one preferred embodiment of the invention, the nucleic acid molecule is isolated from *P. bellina*. The complete cDNA contains 1446 nucleotides and the truncated cDNA contains 1071 nucleotides and encodes a predicted protein of 356 amino acids. The terminus of this protein has characteristic features of a plastid-targeting peptide. It is found that there was only one PbGDPS_LSU detected in *P. bellina* flower. The PbGDPS_LSU showed 35%-45% similarity to GDPS small subunit and 70%-80% similarity to GGDPS. It contained the two conserved aspartate-rich motifs in all members of the prenyltransferase family which are important for substrate binding.

The term "a geranyl diphosphate synthase activity" as referred to herein means ability of condensing dimethylallyl diphosphate and isopentenyl diphosphate (IPP) to geranyl diphosphate. The method for assaying the geranyl diphosphate synthase activity is as described in Burke et al., 2004, Arch Biochem Biophys, 422, 52-60 and Tholl et al., 2004, Plant Cell, 16, 977-992.

The term "a farnesyl diphosphate synthase activity" as referred to herein means ability of transforming geranyl diphosphate and isopentenyl diphosphate to farnesyl diphosphate. The method for assaying the farnesyl diphosphate synthase activity is as described in Burke et al., 2004, Arch Biochem Biophys, 422, 52-60 and Tholl et al., 2004, Plant Cell, 16, 977-992.

In one preferred embodiment of the invention, PbGDPS_LSU protein possessed prenyltransferase activity. The purified protein is assayed using [$^{14}$C]-IPP IPP and DMADP as cosubstrates and MgCl$_2$ as cofactors, and PbGDPS_LSU yields GDP (C$_{10}$) as the major product but also produces the minor product of FDP (C$_{15}$). However, no GGDP (C$_{20}$) is detected with IDP and DMADP as co-substrates. To test the chain-length selectivity of PbGDPS_LSU, either GDP or FDP is added as a substrate together with [$^{14}$C]-IDP. PbGDPS_LSU accepts GDP as the allylic cosubstrate for the production of FDP but can not utilize FDP as the allylic cosubstrate to form GGDP. These results confirmed that PbGDPS possesses prenyltransferase activity with the substrates IDP, DMADP, and GDP. PbGDPS_LSU is able to catalyze the formation of both GDP and FDP. PbGDPS_LSU cDNA is proven to encode for GGDPS protein that behaves bifunctionally and synthesizes GDP as a major product and FDP as a minor product.

In one preferred embodiment of the invention, the gene encoding PbGDPS_LSU is constitutively expressed in all developmental and flowering stages. Spatially, PbGDPS_LSU was strongly expressed in pedicle, petal and to a less extent in root, leaf, sepal and lip but no detectable signal in shoot and column.

As used herein, a polypeptide comprising an amino acid sequence with at least 85% similarity to a reference polypeptide (such as SEQ ID NO: 2) refers to a polypeptide that differ from the reference polypeptide by substitution, deletion or insertion. For example, one or more of an amino acid residue is substituted with another amino acid residue with similar properties (based on size, polarity, hydrophobicity, and the like). The amino acids may be generally categorized into three main classes: hydrophilic amino acids, hydrophobic amino acids and cysteine-like amino acids, depending primarily on the characteristics of the amino acid side chain. These main classes may be further divided into subclasses. Hydrophilic amino acids include amino acids having acidic, basic or polar side chains and hydrophobic amino acids include amino acids having aromatic or apolar side chains. Apolar amino acids may be further subdivided to include, among others, aliphatic amino acids. The definitions of the classes of amino acids as used herein are as follows:

"Hydrophobic Amino Acid" refers to an amino acid having a side chain that is uncharged at physiological pH and that is repelled by aqueous solution. Examples of genetically encoded hydrophobic amino acids include Ile, Leu and Val. Examples of non-genetically encoded hydrophobic amino acids include t-BuA.

"Aromatic Amino Acid" refers to a hydrophobic amino acid having a side chain containing at least one ring having a conjugated π-electron system (aromatic group). The aromatic group may be further substituted with groups such as alkyl, alkenyl, alkynyl, hydroxyl, sulfanyl, nitro and amino groups, as well as others. Examples of genetically encoded aromatic amino acids include Phe, Tyr and Trp. Commonly encountered non-genetically encoded aromatic amino acids include phenylglycine, 2-naphthylalanine, β-2-thienylalanine, 1,2,3,4-tetrahydroisoquinoline-3-carboxylic acid, 4-chloro-phenylalanine, 2-fluorophenylalanine, 3-fluorophenylalanine and 4-fluorophenylalanine.

"Apolar Amino Acid" refers to a hydrophobic amino acid having a side chain that is generally uncharged at physiological pH and that is not polar. Examples of genetically encoded apolar amino acids include Gly, Pro and Met. Examples of non-encoded apolar amino acids include Cha.

"Aliphatic Amino Acid" refers to an apolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Hydrophilic Amino Acid" refers to an amino acid having a side chain that is attracted by aqueous solution. Examples of genetically encoded hydrophilic amino acids include Ser and Lys. Examples of non-encoded hydrophilic amino acids include Cit and hCys.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include Asp and Glu.

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include Arg, Lys and His. Examples of non-genetically encoded basic amino acids include the non-cyclic amino acids ornithine, 2,3-diaminopropionic acid, 2,4-diaminobutyric acid and homoarginine.

"Polar Amino Acid" refers to a hydrophilic amino acid having a side chain that is uncharged at physiological pH, but which has a bond in which the pair of electrons shared in common by two atoms is held more closely by one of the atoms. Examples of genetically encoded polar amino acids include Asx and Glx. Examples of non-genetically encoded polar amino acids include citrulline, N-acetyl lysine and methionine sulfoxide.

"Cysteine-Like Amino Acid" refers to an amino acid having a side chain capable of forming a covalent linkage with a side chain of another amino acid residue, such as a disulfide linkage. Typically, cysteine-like amino acids generally have a side chain containing at least one thiol (SH) group. Examples of genetically encoded cysteine-like amino acids include Cys.

Examples of non-genetically encoded cysteine-like amino acids include homocysteine and penicillamine.

Furthermore, one or more codons encoding a cysteine residue affect a disulfide bond of a specific polypeptide, and thus a cysteine residue is deleted, and the residue can be substituted by another amino acid residue.

As compared with the case in which an amino acid residue is conservatively substituted on the basis of the aforementioned description, when an amino acid residue is arbitrarily substituted, characteristics of the resultant protein are slightly changed.

The site of the aforementioned amino acid sequence at which amino acids are deleted, substituted, or added is arbitrary, so long as a protein containing the resultant modified amino acid sequence exhibits a geranyl diphosphate synthase activity and/or farnesyl diphosphate synthase activity. Similarly, the number of amino acids which are deleted, substituted, or added is arbitrary, so long as a protein composed of the resultant modified amino acid sequence exhibits a geranyl diphosphate synthase activity and/or farnesyl diphosphate synthase activity.

In one preferred embodiment of the invention, the nucleic acid molecule of (d) encodes a polypeptide comprising an amino acid sequence with at least 90%, 95%, 95% or 99% similarity to SEQ ID NO: 2, wherein the polypeptide has a geranyl diphosphate synthase activity and/or farnesyl diphosphate synthase activity. In one more preferred embodiment of the invention, the nucleic acid molecule of (d) encodes a polypeptide comprising an amino acid sequence with at least 99% similarity to SEQ ID NO: 2, wherein the polypeptide has a geranyl diphosphate synthase activity and/or farnesyl diphosphate synthase activity. In one most preferred embodiment, the isolated nucleic acid is PbGDPS_LSU comprising a nucleotide sequence of SEQ ID NO: 1.

Modification (variation) of the aforementioned amino acid sequence may naturally occur through, for example, mutation or modification after translation. A naturally occurring gene (e.g., the PbGDPS_LSU gene of the present invention) may be modified artificially. The present invention encompasses all the modified genes having the aforementioned characteristics, regardless of causes or means for such modification and variation. The gene of the present invention encompasses alleles of the gene encoding a protein composed of the amino acid sequence represented by SEQ ID NO: 1.

Examples of the aforementioned artificial means include genetic engineering methods such as site-specific mutagenesis; chemical synthesis methods such as a phosphate triester method and a phosphate amidite method; and combinations of the above methods. More specifically, synthesis of DNA may be carried out through chemical synthesis by means of a phosphoramidite method or a triester method. Alternatively, synthesis of DNA may be carried out by use of a commercially available automatic oligonucleotide synthesis apparatus. Double-stranded DNA fragments may be produced from single-stranded products which are chemically synthesized by annealing synthesized complementary strands under appropriate conditions or by adding complementary strands by use of an appropriate primer sequence and DNA polymerase.

Specific embodiments of the gene of the present invention include a gene having a nucleotide sequence represented by SEQ ID NO: 1. The nucleotide sequence (coding region) shows an example of the combination of codons corresponding to individual amino acid residues of the amino acid sequence represented by SEQ ID NO: 2. The gene of the present invention is not limited to the gene having such a specific nucleotide sequence; the gene of the present invention may have a nucleotide sequence which is selected from the combinations of arbitrary codons corresponding to individual amino acid residues. Selection of codons may be carried out by means of a customary method. For example, selection of codons may be carried out in consideration of the frequency of use of codons of the host.

The gene of the present invention can be easily produced or obtained by means of a customary genetic engineering method on the basis of sequence information in relation to specific examples of the gene disclosed herein.

The term "complementary" is used herein to refer to the sequences of polynucleotides which is capable of forming Watson & Crick base pairing with another specified polynucleotide throughout the entirety of the complementary region. For the purpose of the present invention, a first polynucleotide is deemed to be complementary to a second polynucleotide when each base in the first polynucleotide is paired with its complementary base. Complementary bases are, generally, A and T (or A and U), or C and G. "Complement" is used herein as a synonym from "complementary polynucleotide", "complementary nucleic acid" and "complementary nucleotide sequence". These terms are applied to pairs of polynucleotides based solely upon their sequences and not any particular set of conditions under which the two polynucleotides would actually bind. Unless otherwise stated, all complementary polynucleotides are fully complementary on the whole length of the considered polynucleotide.

According to the invention, the nucleic acid molecule can be a nucleic acid molecule hybridizes under stringent hybridization conditions to any one of the nucleic acid molecules as defined in (a), (b), (c), (d) and (e). The stringent conditions are not particularly limited, so long as the DNA fragment can be used as a primer or a probe. For example, the hybridization can be carried out under the condition as described above; i.e., in 0.2×SSC containing 0.1% SDS at 60° C., or in 0.1×SSC containing 0.1% SDS at 60° C.

In one preferred embodiment of the invention, the nucleic acid molecule is contained in a vector. The vector is used for storing or producing the nucleic acid molecule, or introducing the nucleic acid molecule into a plant or a plant cell. Preferably, the vector is a shuttle vector. As used herein, the term "shuttle vector" refers to a vector, which can be manipulated and selected in both a plant and a convenient cloning host, such as a prokaryote. Such a shuttle vector may include a kanamycin resistance gene for selection in plant cells and an actinomycin resistance gene for selection in a bacterial host. Besides, the shuttle vector contains an origin of replication appropriate for the prokaryotic host used, and preferably at least one unique restriction site or a polylinker containing unique restriction sites to facilitate the construction.

In another aspect, the nucleic acid molecule according to the invention is preferably driven by a promoter. More preferably, the promoter has an ability to drive expression of a nucleic acid within at least one portion of the reproductive tissues in the recipient plant, such as the cauliflower mosaic virus 35S protein promoter, the α-1 and β-1 tubulin promoter, and the histone promoters. In one embodiment of the invention, the promoter is an inducible promoter comprising but not limited to heat-shock protein promoters and light-inducible promoters including the three chlorophyll a/b light harvesting protein promoters. The methods of vector construction are well known to those skilled in the art.

Another subject of the invention is to provide a cell comprising the isolated nucleic acid molecule mentioned above.

In one preferred embodiment of the invention, the cell is a prokaryotic cell, an eukaryotic cell, a plant cell, a monocot cell, an orchid cell, a *Phalaenopsis* spp. cell, and a cell derived from a protocorn-like body. The term "protocorn-like body" used herein refers to a tissue, which has a potential to differentiate and is an ability for strong and rapid proliferation ability. Preferably, the nucleic acid molecule is introduced to the cell with transformation. As used herein, the term "transformation" refers to a process for changing the genetic material of a cell through introducing a nucleic acid molecule. Persons skilled in this art can conduct the transformation according to the disclosure of the invention and normal knowledge in molecular biology. For example, the vector may be introduced into a bacterial by heat shock process, or the vector is introduced into a plant cell by a gene gun.

Still another subject of the invention is to provide a transgenic plant comprising the nucleic acid molecule mentioned above. Preferably, the transgenic plant is an orchid; more preferably, the transgenic plant is a *Phalaenopsis* spp.

According to the invention, the plants to be transformed with the genes include orchid and orchid cells, preferably *Phalaenopsis* spp., which may be the wild type and an artificial mutant that produced by such as chemical modification, X-ray activated random mutagenesis or recombinant techniques.

Preferably, the transgenic orchid comprising at least one cell transformed with the isolated nucleic acid molecule, which may be transformed by conventional methods known to persons skilled in the art.

In an embodiment of the invention, a transgenic plant can be obtained by regenerating a transformed plant cell with the genes of the invention that are capable of modifying the phenotype of the plant, wherein the cells of the transgenic plant all have the same genetic material. In another embodiment of the invention, a mosaic plant can be obtained by transforming some of cells in a plant, such as reproductive cells or tissues, with the genes of the invention, wherein only the transformed cells express the modified phenotype as compared to the parent plant.

In one preferred embodiment of the invention, a method for producing a transgenic orchid comprising the steps of:
(a) introducing the nucleic acid molecule according to the invention into an orchid cell to obtain an orchid transformed cell; and
(b) regenerating the orchid transformed cell to obtain the transgenic orchid plant.

In one embodiment of the invention, a transgenic orchid plant may be produced through a protocorn-like body in vegetative planting or aspetic seed germination. After separating the cells in a protocorn-like body, each can regenerate a new protocorn-like body and then a new plant. In step (a), the nucleic acid molecule is introduced into a protocorn-like body, and preferably through a gene gun. At this moment, the nucleic acid molecule is introduced into some cells in the protocorn-like body to form transformed cells, and some cells are not introduced with the molecule. The transformed cells can be selected with the marker of the vector. In step (b), the transformed cells are regenerated to transgenic plants. As used herein, the term "regeneration" refers to a growth process of a plant from a plant cell, a group of plant cells or a part of a plant. The method of regeneration is well known to persons skilled in this field. A transgenic orchid produced thereby is also provided in the invention.

Still another subject of the invention is to provide a protein, which protein comprises a polypeptide selected from the group consisting of:
(a) a polypeptide, PbGDPS_LSU, comprising an amino acid sequence of SEQ ID NO: 2;
(b) a polypeptide comprising an amino acid sequence of SEQ ID NO: 2 with one or more of the amino acids have been modified by a deletion, an insertion and/or a substitution, wherein the polypeptide has a geranyl diphosphate synthase activity; and (c) a polypeptide comprising an amino acid sequence with at least 85% similarity to SEQ ID NO: 2, wherein the polypeptide has a geranyl diphosphate synthase activity.

In one preferred embodiment of the invention, the protein has an amino acid sequence of SEQ ID NO: 2.

When a desired gene encoding the protein of the present invention is designed, the nucleotide sequence of the PbGDPS_LSU gene represented by SEQ ID NO: 1 is preferably utilized. If desired, the gene may be designed by appropriately selecting and modifying codons corresponding to the amino acid residues of the protein.

The protein of the present invention may be produced on the basis of the amino acid sequence represented by SEQ ID NO: 2 by means of a general chemical synthesis method. Examples of the synthesis method include a peptide synthesis method employing a usual liquid phase method or a solid phase method.

Specific examples of the peptide synthesis method include a stepwise elongation method in which amino acids are sequentially bound with one another on the basis of amino acid sequence information, to thereby elongate the chain of amino acids; and a fragment condensation method in which fragments composed of several amino acids are synthesized in advance, and the fragments are bound with one another through coupling reaction. The protein of the present invention may be synthesized by means of either of the methods.

In such peptide synthesis, condensation may be carried out by means of a customary method. Examples of the condensation method include an azide method, a mixed acid anhydride method, a DCC method, an active ester method, an oxidation-reduction method, a DPPA (diphenylphosphorylazide) method, a DCC+additive (1-hydroxybenzotriazole, N-hydroxysuccinamide, N-hydroxy-5-norbornane-2,3-dicarboxylmide) method, and a Woodward method.

A solvent employed in such a method can be appropriately selected from widely used solvents used for peptide condensation reaction. Examples of the solvent include dimethylformamide (DMF), dimethylsulfoxide (DMSO), hexaphosphoroamide, dioxane, tetrahydrofuran (THF), ethyl acetate, and solvent mixtures thereof.

In the course of the aforementioned peptide synthesis, a carboxyl group of amino acid or peptide, which group is not involved in the reaction, may be protected typically through esterification, to thereby form esters such as lower alkyl esters; e.g., a methyl ester, an ethyl ester, a tert-butyl ester, and aralkyl esters; e.g., a benzyl ester, a p-methoxybenzyl ester, and a p-nitrobenzyl ester.

An amino acid having a functional group in its side chain; e.g., a hydroxyl group in a tyrosine residue, may be protected with a group such as an acetyl group, a benzyl group, a benzyloxycarbonyl group, or a tert-butyl group. However, the protection may optionally be performed. In addition, for example, a guanidino group in an arginine residue may be protected by an appropriate protective group such as a nitro group, a tosyl group, a p-methoxybenzenesulfonyl group, a methylene-2-sulfonyl group, a benzyloxycarbonyl group, an isobornyloxycarbonyl group, or an adamantyloxycarbonyl group.

Deprotection of these protective groups included in the aforementioned amino acids, peptides, and proteins of the present invention—final products—may be carried out through a routine method; e.g., catalytic reduction or use of a reagent such as liquid ammonia/sodium, hydrogen fluoride, hydrogen bromide, hydrogen chloride, trifluoroacetic acid, acetic acid, formic acid, or methanesulfonic acid.

The thus-obtained protein of the present invention may appropriately be purified through a variety of methods as described above. For example, there may be employed methods generally employed in the field of peptide chemistry; e.g., use of ion-exchange resin, partition chromatography, gel chromatography, and counter current distribution.

The protein of the present invention can be suitably used as an immunogen for producing its specific antibody. By use of the immunogen, a desired antiserum (polyclonal antibody) and monoclonal antibody can be produced.

Still another subject of the invention is to provide a method for improving the production of aroma in a plant, which comprises increasing the expression of the protein mentioned above.

In one embodiment of the invention, the expression of the proteins can be changed by increasing the ploid of the nucleic acid molecule encoding the proteins in at least one cell of the plant. In a preferred embodiment of the invention, a gene gun is used to introduce the nucleic acid molecule into the cell for changing the expression of the protein.

Preferably, the aroma comprises a monoterpene and a precursor thereof. More preferably, the precursor comprises geranyl diphosphate and farnesyl diphosphate.

Still another subject of the invention is to provide a protein complex comprising the protein mentioned and a functional geranyl diphosphate synthase small subunit, wherein the functional geranyl diphosphate synthase small subunit is selected from the group consisting of:

(a) a polypeptide, PbGDPS_SSU, comprising an amino acid sequence of SEQ ID NO: 4;

(b) a polypeptide comprising an amino acid sequence of SEQ ID NO: 4 with one or more of the amino acids have been modified by a deletion, an insertion and/or a substitution, wherein the polypeptide has a geranyl diphosphate synthase activity and/or farnesyl diphosphate synthase; and (c) a polypeptide comprising an amino acid sequence with at least 40% similarity to SEQ ID NO: 4, wherein the polypeptide has a geranyl diphosphate synthase activity and/or farnesyl diphosphate synthase.

Preferably, a functional geranyl diphosphate synthase small subunit comprises an amino acid sequence of SEQ ID NO: 4.

The manner of construction of the polypeptide of (b) and (c) is similar to the aforementioned description.

In one preferred embodiment of the invention, the polypeptide of (c) comprises an amino acid sequence with at least 50%, 60%, 70%, 80%, 90%, 95%, 95% or 99% similarity to SEQ ID NO: 4, wherein the polypeptide has a geranyl diphosphate synthase activity and/or farnesyl diphosphate synthase activity. In one more preferred embodiment of the invention, the polypeptide of (c) comprises an amino acid sequence with at least 90%, 95%, 95% or 99% similarity to SEQ ID NO: 4, wherein the polypeptide has a geranyl diphosphate synthase activity and/or farnesyl diphosphate synthase activity.

In one preferred embodiment of the invention, the protein complex comprises a heterdimer consisting of PbGDPS_LSU and PbGDPS_SSU, wherein PbGDPS_LSU comprises an amino acid sequence of SEQ ID NO: 2 and PbGDPS_SSU comprises an amino acid sequence of SEQ ID NO: 4.

PbGDPS_LSU and PbGDPS_SSU are able to form a heterodimer. Interestingly, PbGDPS_SSU is able to form homodimer, but the homodimeric interaction was not detected for the PbGDPS_LSU. The formation of heterodimer between PbGDPS_LSU and PbGDPS_SSU is the strongest, followed by the PbGDPS_SSU homodimer, and the weakest one is PbGDPS_LSU homodimer. Preferably, the PbGDPS_LSU and PbGDPS_SSU form heterotetramers to function as an active enzyme. To our knowledge, the protein interaction behavior between PbGDPS_LSU and PbGDPS_SSU is not the same as their homologs in eudicots.

Still another subject of the invention is to provide a method for improving the production of aroma in a plant, which comprises increasing the expression of the protein complex mentioned above.

In one preferred embodiment of the invention, combination of PbGDPS_LSU and PbGDPS_SSU has produced the highest GDP and FDP than either PbGDPS_LSU or PbGDPS_SSU per se.

The following Examples are given for the purpose of illustration only and are not intended to limit the scope of the present invention.

EXAMPLE

Materials and Methods

Plant Materials

*P. bellina* flowers were grown under standard greenhouse conditions as described previously (Hsiao et al., 2006, BMC Plant Biol, 6, 14).

5' and 3' Amplification of PbGDPS Large Subunit (PbGDPS_LSU) cDNA Ends

The full-length PbGDPS_LSU cDNA was obtained by extending the 5' and 3' ends of the cDNA using the SMART RACE cDNA amplification kit (Clontech; Palo Alto, Calif.). The cDNA containing the 5' and 3' end for PbGDPS_LSU clones were obtained by PCR amplification with use of a 5' or 3' universal primer and 3' or 5' gene-specific nested primer, respectively (Clontech). The PbGDPS_LSU gene specific primers: 5'-s CGAGGAGGGAGTATCGCATCGCTTCGT-3' (SEQ ID NO: 5) was used to amplify the 5' end fragments and 5'-CACACCATGTCTCTCATCCACGACGATC-3' (SEQ ID NO: 6) was used to amplify the 3' end fragments. The PCR products were cloned into the pGEM-T Easy vector (Promega; Madison, Wis.) and both strands from 10 positive clones were sequenced.

Sequences Analysis

Sequence data used in this study were downloaded from the EMBL/GenBank data libraries under the following accession numbers: *Antirrhinum majus* GDPS small subunit (GDPS_Antirrhinum_SSU), AY534686; *Clarkia breweri* GDPS small subunit (GDPS_Clarkia_SSU), AY534745; *Mentha piperita* GDPS small subunit (GDPS_Mentha_SSU), AF182827; *M. piperita* GDPS large subunit (GDPS_Mentha_LSU), AF182828; *A. majus* GDPS large subunit (GDPS_Antirrhinum_LSU), AY534687; *Lycopersicon esculentum* GDPS, DQ2869302; *Quercus robur* GDPS, CAC20852; *Vitis vinifera* GDPS, Am457037; *Arabidopsis* GDPS, Y17376; *Abies grandis* GDPS, AF513111, AF513112, AF513112; *Citrus sinensis* GDPS, AJ243739; *Arabidopsis* GGDPS1, NP_195399; *Capsicum annuum* GGDPS, X80267; *A. grandis* GGDPS, AF425235; *Oryza sativa* GGDPS, CM000132.1; *Croton sublyratus* GGDPS, AB034249.1; *Gentiana lutea* GGDPS, AB028667.1; *V. vinifera* GGDPS, AM438997.2; *Scoparia dulcis* GGDPS, AB034250.1; *Helianthus annuus* GGDPS, AF020041.1; *Sinapis Alba* GGDPS, 2J1P_A; *Lupinus albus* FDPS, U15777; *Artemisia annua* FDPS, U36376; *Arabidopsis* FDPS1, NM_124151; *C. annuum* FDPS, X84695; *O. sativa* FDPS, NM_192229; and *Zea mays* FDPS, L39789.

Expression of His-Tagged PbGDPS_LSU and PbGDPS_LSU/PbGDPS_SSU Recombinant Protein A truncated version of PbGDPS_LSU, in which the N-terminal plastid targeting sequence was deleted, was obtained using the forward primer 5'-CACCATGCCCTCTGTTGCCACAACCGAGT-3' (SEQ ID NO: 7) which introduced a starting Met in place of Pro-26, and the reverse primer 5'-ATTCTGCCTGTAAGCGATGTAATTCGCA-3' (SEQ ID NO: 8) for subcloning into the pBAD/D-TOPO directional expression vector (Invitrogen, Carlsbad, Calif.). To express N-terminally His-tagged PbGDPS_LSU recombinant protein, *E. coli* BL21 (DE3) pLysS cells were transformed with the resulting recombinant plasmid. The empty pBAD202/D-TOPO vector was also transformed into BL21 (DE3) pLysS cells to serve as a negative control. Single positive bacterial colonies were inoculated into 30-50 ml and grown overnight at 37° C. and transfer the inoculated culture into a large volume of medium until an $OD_{600}$ of 0.5 was reached. Cultures were then induced by the addition of L-arabinose (Sigma) to a final concentration of 0.1% and allowed to grow for an additional 5 h at 17° C. for the induction of protein expression. For coexpression, BL21 (DE3) pLysS *E. coli* cells were cotransformed with two plasmids PbGDPS_LSU and PbGDPS_SSU (Hsiao et al., 2008, Plant J, 55, 719-733) in a single transformation event. Single positive bacterial colonies were used to inoculate Luriabertani medium with 100 µg/ml of ampicillin (pET15b, Hsiao et al., 2008, Plant J, 55, 719-733) and 50 µg/ml of kanamycin (pBAD202), which was induced by the addition of 0.1% L-arabinose and 0.05 mM isopropyl-1-thio-β-D-galactopyranoside.

RT-PCR

Total RNA was extracted from the developing flowers of *P. bellina*, from flower buds to day 14 post-anthesis (senescence). cDNA was synthesized using DNase-treated total RNA, an oligo dT primer and SuperScriptIII reverse transcriptase (Invitrogen, Carlsbad, Calif.) according to the manufacturer's protocol. The optimal gene-specific primers used to amplify the PbGDPS_LSU sequence for the RT-PCR were 5'-GGCTAGCAACAAGACAACCT-3' (forward) (SEQ ID NO: 9) and 5'-GAAATTTGAAGCAGCCTAGC-3' (reverse) (SEQ ID NO: 10). PCR with the actin gene-specific primers of *Phalaenopsis* (Hsiao et al., 2008, Plant J, 55, 719-733) was performed. To ensure that an equal amount of RNA was used for all samples and that RT reactions were equally effective.

Yeast Two-Hybrid Analysis

Yeast two-hybrid analysis was performed using the MATCHMAKER yeast two-hybrid system (Clontech, Palo Alto, Calif.). PCR was used to generate a sequence that was flanked by EcoR1 sites and that encoded the same truncated version of PbGDPS_LSU as used for the recombinant His-tagged protein. This PCR product was cloned into the binding domain vector pGBKT7 and the activation domain vector pGADT7. Introduction of the inserts in the correct reading frame was confirmed by sequencing. The resulting constructs were transformed into yeast strain AH109 by the lithium acetate method. The transformants that received both the DNA binding domain plasmid and the activation domain plasmid were selected on medium lacking adenine, histidine, leucine and tryptophan according to the instructions of the manufacturer of the yeast two-hybrid system.

For quantification the interaction strength between GDPS proteins, the colony-lift filter assays were used for β-galactosidase activity. The colony-lift filter assay was performed according to the manufacturer's instructions (Clontech). For the analysis of β-galactosidase activity, yeast strain Y187 was used (Clontech).

Results

Molecular Cloning and Sequence Analysis of PbGDPS_LSU

Figure 1A:
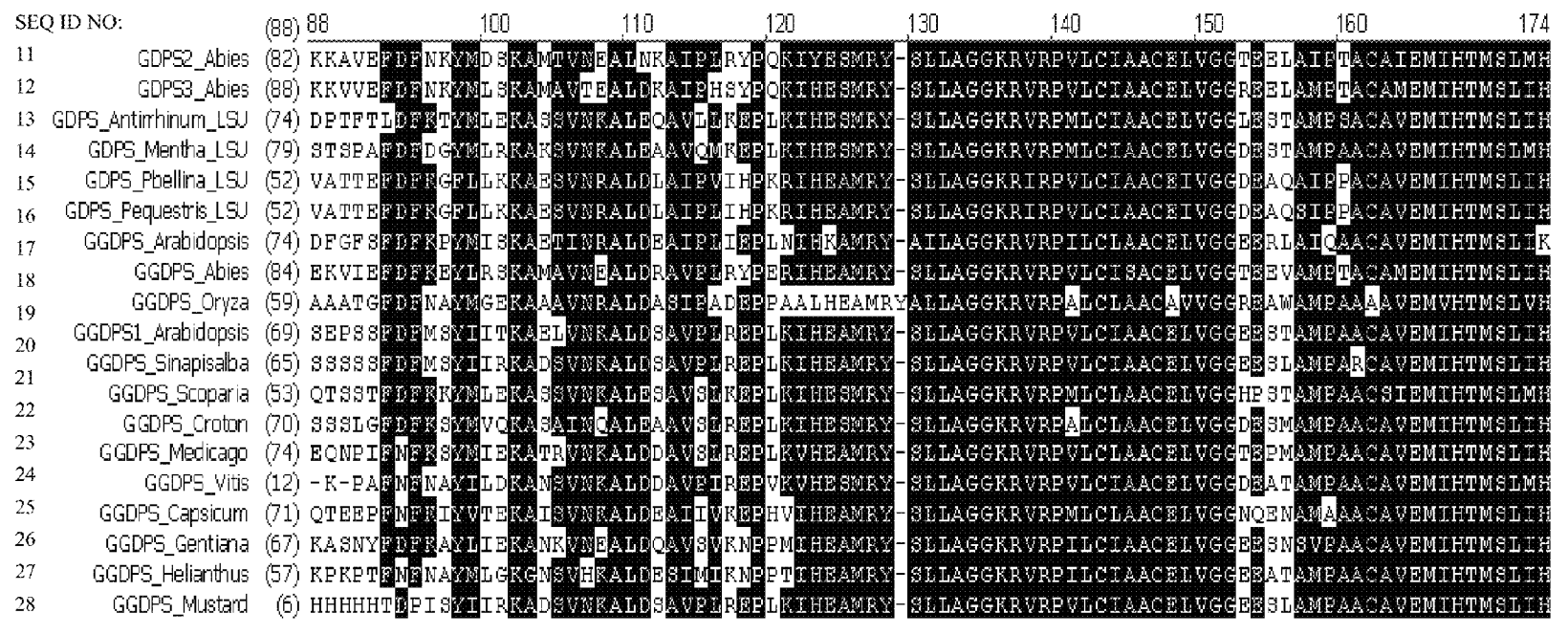
Figure 1B:
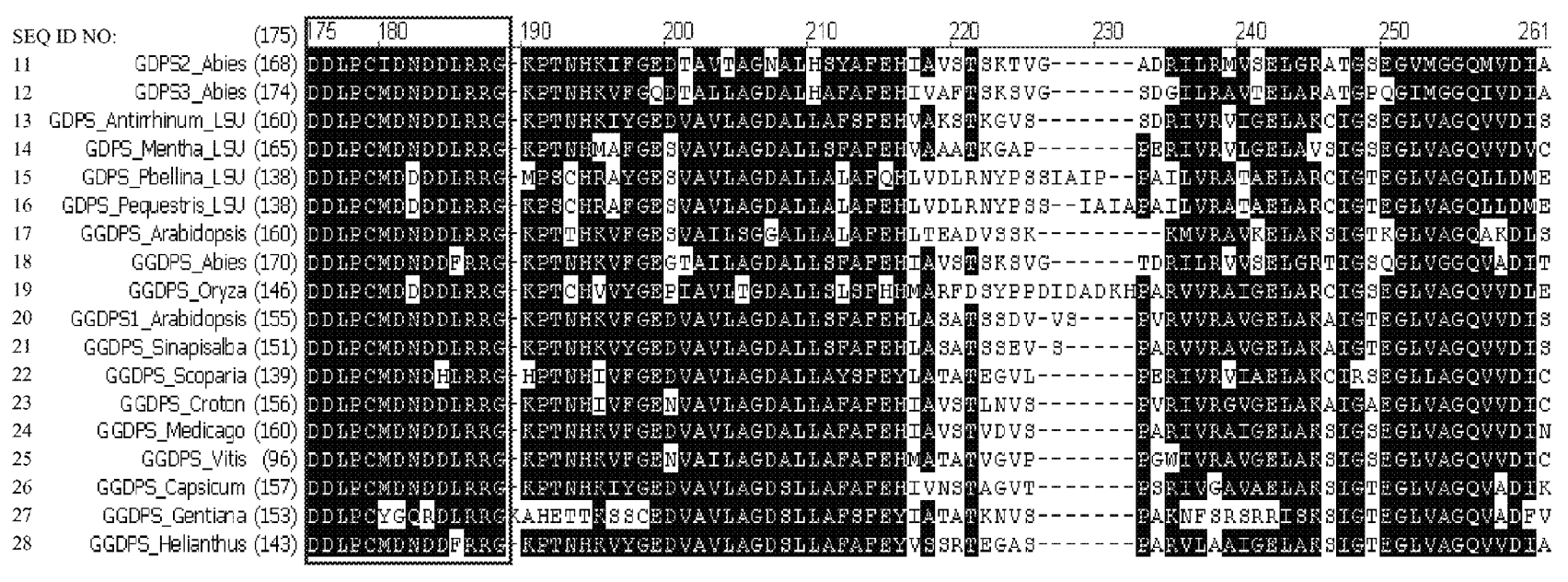
Figure 1C:
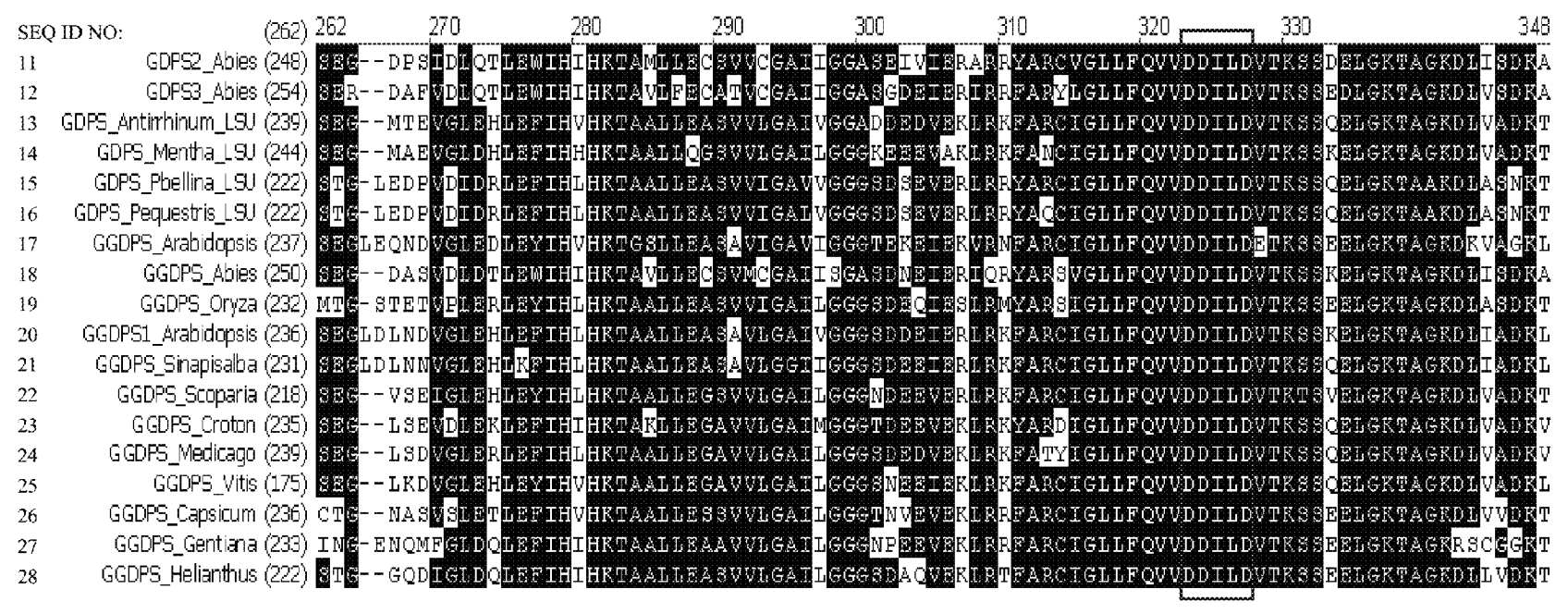

The partial cDNA of *P. bellina* GDPS large subunit (PbGDPS_LSU) was isolated from a *P. bellina* floral cDNA library (Hsiao et al., 2006, BMC Plant Biol, 6, 14). A full-length cDNA was obtained by 5' and 3' rapid amplification of cDNA ends (RACE). The complete cDNA contains 1446 nucleotides and the truncated cDNA contains 1071 nucleotides and encodes a predicted protein of 356 amino acids (FIG. 1). The terminus of this protein has characteristic features of a plastid-targeting peptide. Several plant species contain multiple GGDPS and GGDPS-related enzymes (Burke and Croteau, 2002, Arch Biochem Biophys, 405, 130-136). To confirm the PbGDPS_LSU existed in floral of *P. bellina*, the presence of other PbGDPS_LSU and GGDPS in various developmental stages as well as flower on flowering day (D-day) and the day 5 post-anthesis (D+5) by using PCR-based cloning methods is searched. The search results revealed that there was only one PbGDPS_LSU detected in *P. bellina* flower. The PbGDPS_LSU showed 35%-45% similarity to GDPS small subunit (*M. piperita, A. majus, C. breweri* and *P. bellina*) and 70%-80% similarity to GGDPS (Table 1; FIG. 1). It contained the two conserved aspartate-rich motifs (FIG. 1, blue box) in all members of the prenyltransferase family which are important for substrate binding (Wang and Ohnuma, 2000, Biochim Biophys Acta, 1529, 33-48). According to this homology, the PbGDPS_LSU may function as GGDPS.

TABLE 1

Percentage of amino acid similarity at full length sequence of short chain prenyltransferase from different plants

|  | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| 1 GDPS_Phal_SSU |  | 48 | 48 | 50 | 48 | 28 | 24 | 26 | 25 | 24 | 22 | 25 | 25 | 25 | 39 | 36 | 36 |
| 2 GDPS_Antirrhinum_SSU |  |  | 73 | 68 | 61 | 25 | 26 | 30 | 27 | 26 | 25 | 34 | 33 | 31 | 45 | 44 | 44 |
| 3 GDPS_Mentha_SSU |  |  |  | 67 | 58 | 24 | 25 | 29 | 26 | 26 | 23 | 31 | 33 | 32 | 44 | 44 | 42 |
| 4 GDPS_Vitis |  |  |  |  | 61 | 28 | 25 | 30 | 26 | 27 | 25 | 31 | 31 | 28 | 46 | 46 | 43 |
| 5 GDPS_Clarkia_SSU |  |  |  |  |  | 24 | 23 | 24 | 22 | 25 | 25 | 30 | 31 | 30 | 44 | 44 | 42 |
| 6 FDPS_Arabidopsis |  |  |  |  |  |  | 91 | 86 | 87 | 85 | 26 | 30 | 31 | 31 | 31 | 31 | 33 |
| 7 FDPS_Lupinus |  |  |  |  |  |  |  | 91 | 87 | 86 | 27 | 29 | 30 | 30 | 33 | 30 | 33 |
| 8 FDPS_Artemisia |  |  |  |  |  |  |  |  | 85 | 85 | 27 | 33 | 33 | 34 | 34 | 30 | 34 |
| 9 FDPS_Capsicum |  |  |  |  |  |  |  |  |  | 83 | 26 | 29 | 31 | 30 | 34 | 32 | 34 |
| 10 FDPS_Oryza |  |  |  |  |  |  |  |  |  |  | 27 | 29 | 31 | 29 | 32 | 30 | 32 |
| 11 FDPS_Zea |  |  |  |  |  |  |  |  |  |  |  | 29 | 30 | 29 | 33 | 31 | 33 |
| 12 GDPS_Arabidopsis |  |  |  |  |  |  |  |  |  |  |  |  | 91 | 82 | 36 | 38 | 38 |
| 13 GDPS_Citrus |  |  |  |  |  |  |  |  |  |  |  |  |  | 95 | 42 | 42 | 41 |
| 14 GDPS_Tomato |  |  |  |  |  |  |  |  |  |  |  |  |  |  | 36 | 36 | 36 |
| 15 GGDPS_Abies |  |  |  |  |  |  |  |  |  |  |  |  |  |  |  | 80 | 77 |
| 16 GDPS2_Abies |  |  |  |  |  |  |  |  |  |  |  |  |  |  |  |  | 80 |
| 17 GDPS3_Abies |  |  |  |  |  |  |  |  |  |  |  |  |  |  |  |  |  |
| 18 GGDPS_Oryza |  |  |  |  |  |  |  |  |  |  |  |  |  |  |  |  |  |
| 19 GGDPS1_Arabidopsis |  |  |  |  |  |  |  |  |  |  |  |  |  |  |  |  |  |
| 20 GGDPS_Sinapisalba |  |  |  |  |  |  |  |  |  |  |  |  |  |  |  |  |  |
| 21 GGDPS_Arabidopsis |  |  |  |  |  |  |  |  |  |  |  |  |  |  |  |  |  |
| 22 GDPS_Antirrhinum_LSU |  |  |  |  |  |  |  |  |  |  |  |  |  |  |  |  |  |
| 23 GGDPS_Sooparia |  |  |  |  |  |  |  |  |  |  |  |  |  |  |  |  |  |
| 24 GDPS_Mentha_LSU |  |  |  |  |  |  |  |  |  |  |  |  |  |  |  |  |  |
| 25 GGDPS_Croton |  |  |  |  |  |  |  |  |  |  |  |  |  |  |  |  |  |
| 26 GGDPS_Medicago |  |  |  |  |  |  |  |  |  |  |  |  |  |  |  |  |  |
| 27 GGDPS_Vitis |  |  |  |  |  |  |  |  |  |  |  |  |  |  |  |  |  |
| 28 GGDPS_Capsicum |  |  |  |  |  |  |  |  |  |  |  |  |  |  |  |  |  |
| 29 GGDPS_Gentiana |  |  |  |  |  |  |  |  |  |  |  |  |  |  |  |  |  |
| 30 GGDPS_Helianthus |  |  |  |  |  |  |  |  |  |  |  |  |  |  |  |  |  |
| 31 GGDPS_Mustard |  |  |  |  |  |  |  |  |  |  |  |  |  |  |  |  |  |
| 32 GDPS_Pbellina_LSU |  |  |  |  |  |  |  |  |  |  |  |  |  |  |  |  |  |
| 33 GDPS_Pequestris_LSU |  |  |  |  |  |  |  |  |  |  |  |  |  |  |  |  |  |

|  | 18 | 19 | 20 | 21 | 22 | 23 | 24 | 25 | 26 | 27 | 28 | 29 | 30 | 31 | 32 | 33 |
|---|---|---|---|---|---|---|---|---|---|---|---|---|---|---|---|---|
| 1 GDPS_Phal_SSU | 37 | 40 | 40 | 39 | 41 | 39 | 37 | 38 | 36 | 40 | 36 | 36 | 39 | 41 | 37 | 37 |
| 2 GDPS_Antirrhinum_SSU | 43 | 49 | 48 | 48 | 49 | 46 | 44 | 46 | 45 | 47 | 46 | 46 | 46 | 51 | 44 | 45 |
| 3 GDPS_Mentha_SSU | 42 | 48 | 47 | 46 | 45 | 47 | 46 | 46 | 45 | 48 | 44 | 43 | 45 | 49 | 43 | 44 |
| 4 GDPS_Vitis | 43 | 48 | 47 | 48 | 48 | 47 | 46 | 48 | 46 | 48 | 46 | 45 | 46 | 52 | 42 | 43 |
| 5 GDPS_Clarkia_SSU | 46 | 48 | 48 | 48 | 46 | 46 | 44 | 47 | 46 | 48 | 48 | 42 | 45 | 52 | 45 | 45 |
| 6 FDPS_Arabidopsis | 31 | 30 | 30 | 30 | 32 | 32 | 31 | 32 | 32 | 34 | 29 | 29 | 32 | 32 | 31 | 32 |
| 7 FDPS_Lupinus | 30 | 31 | 31 | 32 | 33 | 30 | 31 | 31 | 32 | 32 | 31 | 29 | 32 | 30 | 30 | 31 |
| 8 FDPS_Artemisia | 32 | 32 | 33 | 34 | 33 | 33 | 33 | 32 | 33 | 34 | 33 | 30 | 33 | 32 | 32 | 32 |
| 9 FDPS_Capsicum | 33 | 32 | 32 | 32 | 33 | 31 | 32 | 32 | 33 | 33 | 32 | 30 | 33 | 31 | 32 | 33 |
| 10 FDPS_Oryza | 32 | 32 | 32 | 33 | 33 | 32 | 32 | 33 | 33 | 33 | 31 | 31 | 32 | 32 | 32 | 32 |
| 11 FDPS_Zea | 32 | 33 | 34 | 33 | 34 | 33 | 33 | 33 | 33 | 34 | 30 | 32 | 33 | 33 | 32 | 33 |
| 12 GDPS_Arabidopsis | 42 | 41 | 41 | 37 | 41 | 40 | 39 | 40 | 40 | 40 | 39 | 40 | 46 | 42 | 42 | 42 |
| 13 GDPS_Citrus | 43 | 47 | 46 | 43 | 44 | 44 | 44 | 43 | 44 | 45 | 44 | 42 | 44 | 46 | 44 | 44 |
| 14 GDPS_Tomato | 39 | 41 | 41 | 36 | 40 | 41 | 38 | 38 | 40 | 43 | 39 | 38 | 38 | 44 | 41 | 41 |
| 15 GGDPS_Abies | 65 | 70 | 70 | 67 | 72 | 73 | 67 | 72 | 72 | 80 | 71 | 65 | 72 | 79 | 71 | 72 |
| 16 GDPS2_Abies | 65 | 71 | 73 | 64 | 71 | 72 | 66 | 71 | 69 | 81 | 69 | 62 | 71 | 79 | 71 | 72 |
| 17 GDPS3_Abies | 64 | 70 | 70 | 64 | 68 | 69 | 65 | 69 | 68 | 78 | 68 | 60 | 69 | 78 | 69 | 70 |
| 18 GGDPS_Oryza |  | 70 | 72 | 66 | 70 | 71 | 69 | 73 | 70 | 78 | 70 | 65 | 69 | 79 | 72 | 72 |

TABLE 1-continued

Percentage of amino acid similarity at full length sequence of short chain prenyltransferase from different plants

| | | | | | | | | | | | | | | |
|---|---|---|---|---|---|---|---|---|---|---|---|---|---|---|
| 19 GGDPS1_Arabidopsis | 88 | 74 | 78 | 82 | 78 | 80 | 80 | 91 | 74 | 70 | 76 | 93 | 76 | 77 |
| 20 GGDPS_Sinapisalba | | 76 | 78 | 81 | 77 | 79 | 80 | 90 | 74 | 71 | 76 | 95 | 76 | 77 |
| 21 GGDPS_Arabidopsis | | | 70 | 73 | 69 | 72 | 72 | 82 | 69 | 66 | 72 | 83 | 71 | 71 |
| 22 GDPS_Antirrhinum_LSU | | | | 83 | 77 | 79 | 78 | 88 | 76 | 70 | 77 | 86 | 74 | 74 |
| 23 GGDPS_Sooparia | | | | | 81 | 83 | 81 | 88 | 77 | 72 | 76 | 88 | 74 | 75 |
| 24 GDPS_Mentha_LSU | | | | | | 79 | 76 | 88 | 72 | 67 | 74 | 85 | 73 | 73 |
| 25 GGDPS_Croton | | | | | | | 83 | 90 | 75 | 74 | 75 | 87 | 74 | 75 |
| 26 GGDPS_Medicago | | | | | | | | 91 | 75 | 72 | 76 | 88 | 74 | 75 |
| 27 GGDPS_Vitis | | | | | | | | | 85 | 80 | 86 | 91 | 81 | 82 |
| 28 GGDPS_Capsicum | | | | | | | | | | 70 | 78 | 85 | 75 | 75 |
| 29 GGDPS_Gentiana | | | | | | | | | | | 71 | 83 | 70 | 70 |
| 30 GGDPS_Helianthus | | | | | | | | | | | | 85 | 73 | 73 |
| 31 GGDPS_Mustard | | | | | | | | | | | | | 84 | 84 |
| 32 GDPS_Pbellina_LSU | | | | | | | | | | | | | | 98 |
| 33 GDPS_Pequestris_LSU | | | | | | | | | | | | | | |

Functional Characterization of Recombinant PbGDPS_LSU

In previous studies of GDPS and GGDPS, optimal expression of soluble recombinant enzyme was only obtained after deleting the N-terminal plastid targeting sequence (Burke and Croteau, 2002, Arch Biochem Biophys, 405, 130-136; Burke and Croteau, 2002, J Biol Chem, 277, 3141-3149). Recombinant PbGDPS showed the same characteristics. When full-length PbGDPS was expressed in E. coli, very little soluble protein was obtained, and the majority of the expressed protein formed was located in inclusion bodies. To overcome this problem, a truncated version of the PbGDPS_LSU open reading frame was cloned, which lacked the N-terminal signal sequence and its calculated molecular weight was 50 kD (FIG. 2A). To assay whether the recombinant truncated PbGDPS_LSU protein possessed prenyltransferase activity, the purified protein was assayed using [14C]-IPP and DMADP as cosubstrates and MgCl2 as cofactors. The resulting products were further hydrolyzed to the corresponding alcohols and then analyzed by using thin-layer chromatography and scintillation counting of the radioactive areas (TLC; FIG. 2B). Recombinant truncated PbGDPS_LSU yielded GDP (C10) as the major product but also produced the minor product of FDP (C15) (FIG. 2B). However, no GGDP (C20) was detected by radioactive TLC with IDP and DMADP as co-substrates. To test the chain-length selectivity of PbGDPS_LSU, either GDP or FDP was added as a substrate together with [14C]-IDP. PbGDPS_LSU could accept GDP as the allylic cosubstrate for the production of FDP but could not utilize FDP as the allylic cosubstrate to form GGDP (FIG. 2B). These results confirmed that PbGDPS possesses prenyltransferase activity with the substrates IDP, DMADP, and GDP. In the negative control experiments, the boiled protein (FIG. 2B) and the empty vector (data not shown) did not produce any products. Thus, this PbGDPS_LSU was able to catalyze the formation of both GDP and FDP. is PbGDPS_LSU cDNA is proven to encode for GGDPS protein that behaves bifunctionally and synthesizes GDP as a major product and FDP as a minor product.

Analysis of the Spatial and Temporal Expression of PbGDPS_LSU

Figure 3:
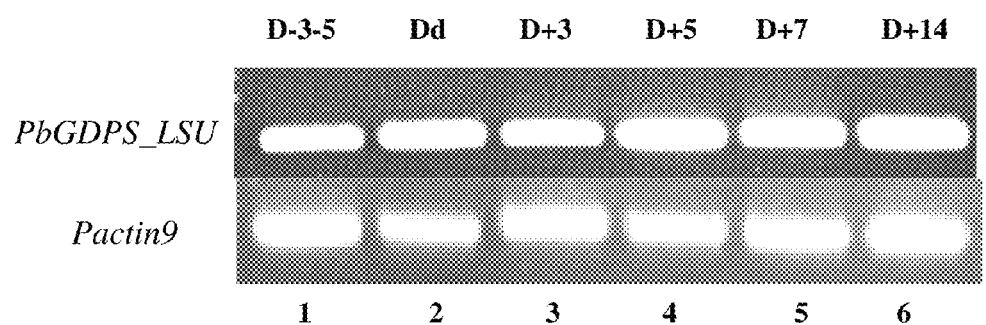
FIG. 3 illustrates expression analysis of PbGDPS_LSU transcripts in flower from day 5 pre-anthesis (D-5), flowering day (Dd) to day 14 post-anthesis (D+14; flower senescence) (lanes 1~6) and different tissues (lanes 1~8). (A) RT-PCR analysis of PbGDPS_LSU with gene-specific primers was performed on RNA isolated from day 5 pre-anthesis to post-anthesis of flower. Pactin9 gene was used as an internal control. (B) Spatial expression of PbGDPS_LSU with gene-specific primers was analyzed on RNA isolated from root, shoot, leaf, pedicle, sepal, petal, lip and column. Pactin9 gene was used as an internal control.
Figure 3:
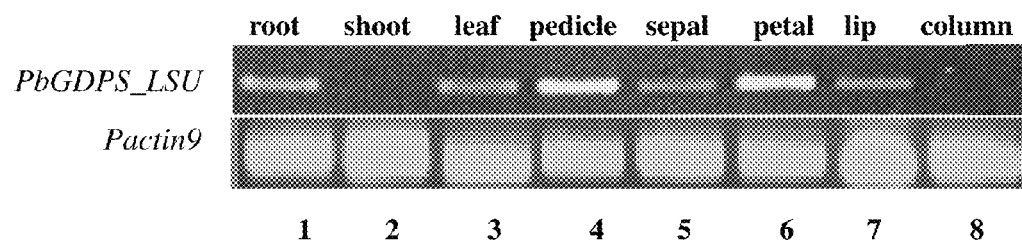

To understand when and where PbGDPS_LSU was active, we examined both the temporal and spatial expression of the gene by use of the 3' specific primer. Result showed the gene encoding PbGDPS_LSU was constitutively expressed in all developmental and flowering stages (FIG. 3A, lanes 1~6). Spatially, PbGDPS_LSU was strongly expressed in pedicle, petal (lane 4~6) and to a less extent in root, leaf, sepal and lip (lanes 1, 3, 5 and 7) but no detectable signal in shoot and column (FIG. 3B, lane 2 and lane 8). It revealed that the expression pattern of PbGDPS_LSU did not correlate well with the monoterpene emission.

Interaction of PbGDPS_LSU and PbGDPS_SSU

Figure 4:
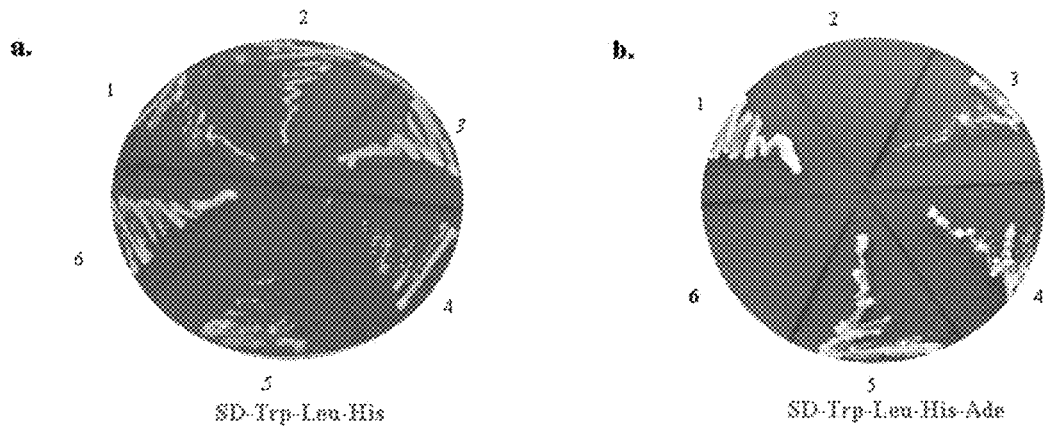
FIG. 4A illustrates interaction between PbGDPS proteins (LSU and SSU) in yeast as detected by two-hybrid system. Left panel: yeast strains AH109 co-transformed with both binding and activation vectors containing PbGDPS large subunit and small subunit combinations represented by numbers were streaked on the Minimal Synthetic Dropout (SD) medium without 1 leucine, tryptophan and histidine (a). Right panel: yeast strains relative to those in the left panel were streaked on the SD medium without adenine, histidine, leucine and tryptophan. (b). 1, pGBKT7-PbGDPS_SSU+pGADT7—PbGDPS_SSU; 2, pGBKT7-PbGDPS_LSU+pGADT7—PbGDPS_LSU; 3, pGBKT7-PbGDPS_SSU+pGADT7—PbGDPS_LSU; 4, pGBKT7-PbGDPS_LSU+pGADT7—PbGDPS_SSU; 5, pGADT7-T+pGBKT7-53 (positive control); 6, pGADT7-PbGDPS_SSU+pGBKT7 (negative control).
FIG. 4B illustrates the yeast two-hybrid assay showing the relative interaction strength between PbGDPS_LSU and PbGDPS_SSU proteins. Activation of HIS3 and lacZ was indicated by growth on −HIS media with 20 mM 3AT.
Figure 4:

For understanding how PbGDPS_LSU and PbGDPS_SSU function in orchids, the interaction between these LSU and SSU of PbGDPS by using an Y2H system is analyzed, the standard way to identify in vivo protein-protein interactions. The PbGDPS_LSU and PbGDPS_SSU open reading frames were cloned into the DNA-binding-domain vector pGBKT7 and activation-domain vector pGADT7, respectively. Combination of vector containing PbGDPS_LSU or PbGDPS_SSU cDNA was then introduced into yeast, and the interactions between these proteins were assessed by growing colonies on medium lacking adenine and histidine (SD-Trp-Leu-His-Ade). As expected, PbGDPS_LSU and PbGDPS_SSU formed heterodimer as similar to those of eudicots. Interestingly, the PbGDPS_SSU was able to form homodimeric interaction, but the homodimeric interaction was not detected for the PbGDPS_LSU (FIG. 4A). The relative protein-protein interaction strength was assessed by using colony-lift filter assay. Results showed that the formation of heterodimer between PbGDPS_LSU and PbGDPS_SSU was the strongest, followed by the PbGDPS_SSU homodimer, and the weakest one was PbGDPS_LSU homodimer (FIG. 4B). These results suggested that the PbGDPS_LSU and PbGDPS_SSU might form heterotetramers to function as an active enzyme. To our knowledge, the protein interaction behavior between PbGDPS_LSU and PbGDPS_SSU was not the same as their homologs in eudicots.

Figure 5:
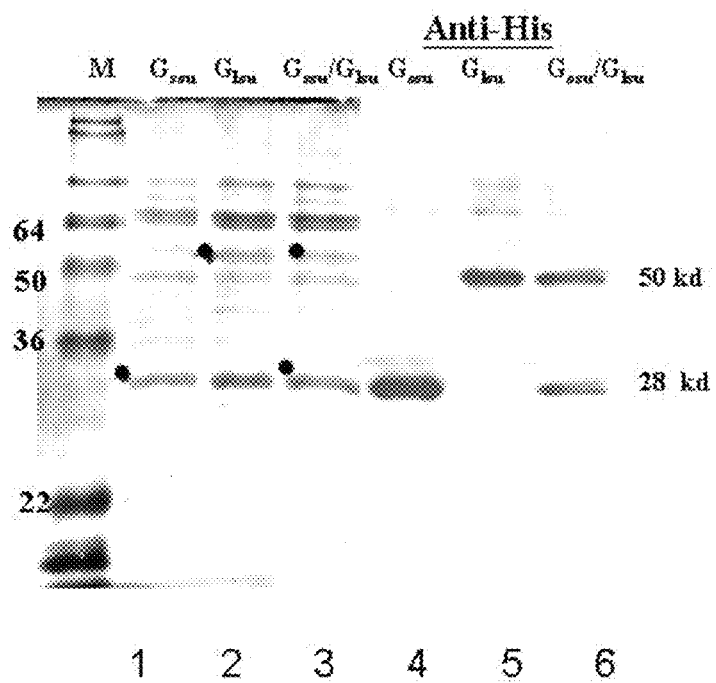
FIG. 5 illustrates enzyme activity of PbGDPS_LSU/PbGDPS_SSU. (A) Expression of recombinant PbGDPS_SSU, PbGDPS_LSU and PbGDPS_LSU/PbGDPS_SSU. Partial purified His-tagged PbGDPS_SSU, PbGDPS_LSU and PbGDPS_LSU/PbGDPS_SSU from *E. coli* (lanes 1~3), and western blot with anti-His tag antibody (lanes 4~6). The black circles indicate the position of the recombinant protein. Molecular mass markers are indicated on the left margin. (B) Prenyltransferase activity of purified recombinant PbGDPS_SSU, PbGDPS_LSU and PbGDPS_LSU/Pb- GDPS_SSU protein (100 μg) with Mg$^{2+}$ (10 mM). Boiled protein was included as a negative control in the same assay. Each point column represents the average of values from three independent experiments. Vertical bars indicate standard errors. (C) Quantification of the products derived by enzymatic hydrolysis of prenyl diphosphate products shown on radioactive TLC analysis. The purified recombinant PbGDPS_SSU, PbGDPS_LSU and PbGDPS_LSU/Pb-GDPS_SSU was using various prenyldiphosphates with different chain lengths as substrates as well as [4-$^{14}$C]IPP, DMADP, GDP, and FDP. The experiment was repeated for three times independently.
Figure 5:
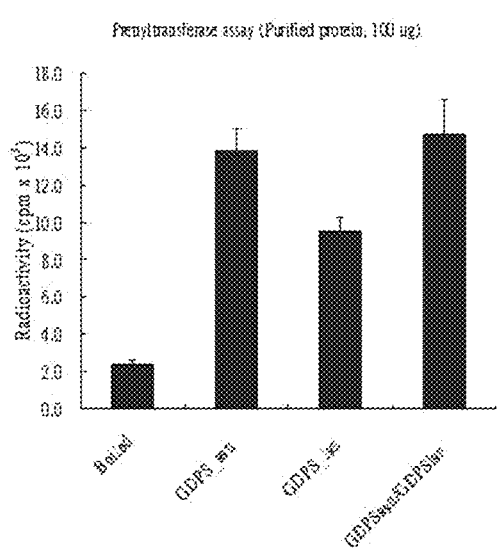
Figure 5:
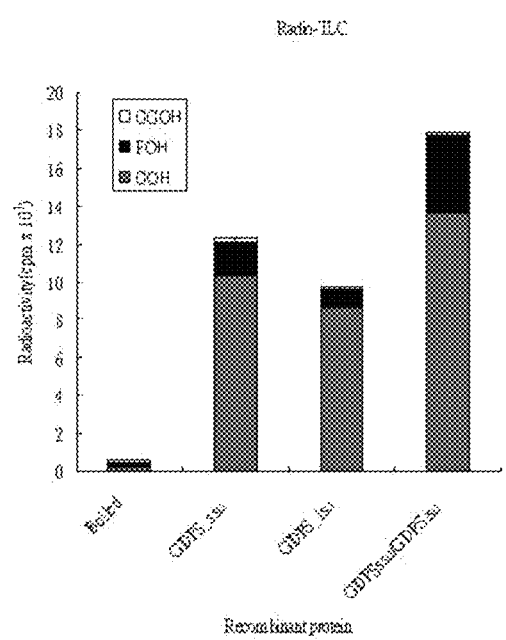

Functional Characterization of Recombinant PbGDPS Large Subunit with PbGDPS Small Subunit Previous studies of PbGDPS_LSU and PbGDPS_SSU indicated that the protein function was to produce GDP and FDP, respectively. Coexpression of the PbGDPS_LSU and PbGDPS_SSU (FIG. 5A) revealed higher prenyltransferase activity than either PbGDPS_LSU or PbGDPS_SSU alone (FIG. 5B). The resulting products were further hydrolyzed to the corresponding alcohols and then analyzed by thin-layer chromatography and scintillation counting of the radioactive areas (TLC; FIG. 5C). Results showed combination of PbGDPS_LSU and PbGDPS_SSU has produced the highest GDP and FDP than either PbGDPS_LSU or PbGDPS_SSU per se (FIG. 5C).

While embodiments of the present invention have been illustrated and described, various modifications and improvements can be made by persons skilled in the art. The present invention is not limited to the particular forms as illustrated, and that all the modifications not departing from the spirit and scope of the present invention are within the scope as defined in the appended claims.

What is claimed is:

1. An isolated nucleic acid molecule comprising the nucleotide sequence of SEQ ID NO: 1.
2. A vector comprising the isolated nucleic acid molecule according to claim 1.
3. The vector according to claim 2, which is a shuttle vector that is capable of expressing the nucleic acid molecule in a plant.
4. The vector according to claim 2, which comprises an inducible promoter.
5. A cell transformed by the vector according to claim 2.
6. The cell according to claim 5, which is selected from the group consisting of a prokaryotic cell, an eukaryotic cell, a plant cell, a monocot cell, an orchid cell, a *Phalaenopsis* spp. cell, and a cell derived from a protocorm-like body.
7. A transgenic plant comprising the nucleic acid molecule according to claim 1.
8. The transgenic plant according to claim 7, which is an orchid.
9. The transgenic plant according to claim 8, which is a *Phalaenopsis* spp.

* * * * *